US008876692B2

(12) United States Patent
Genovesi

(10) Patent No.: US 8,876,692 B2
(45) Date of Patent: Nov. 4, 2014

(54) METHOD AND DEVICE FOR PRESERVING THE VITALITY AND FUNCTION OF A HARVESTED BLOOD VESSEL

(76) Inventor: Mark Genovesi, New Rochelle, NY (US)

(*) Notice: Subject to any disclaimer, the term of this patent is extended or adjusted under 35 U.S.C. 154(b) by 242 days.

(21) Appl. No.: 13/506,091

(22) Filed: Mar. 26, 2012

(65) Prior Publication Data
US 2013/0017532 A1    Jan. 17, 2013

Related U.S. Application Data

(63) Continuation-in-part of application No. 11/653,528, filed on Jan. 16, 2007, now Pat. No. 8,162,815.

(51) Int. Cl.
*A61F 2/06* (2013.01)
*A01N 1/02* (2006.01)

(52) U.S. Cl.
CPC .............. *A01N 1/02* (2013.01); *A01N 1/0247* (2013.01); *A61F 2/062* (2013.01)
USPC .......................................................... 600/36

(58) Field of Classification Search
CPC ...... A61F 2/02; A61F 2/04; A61F 2/06–2/07; Y10S 623/916; Y10S 623/92
USPC .................... 600/36; 623/1.1–1.54; 206/438; 435/283.1–309.4
See application file for complete search history.

(56) References Cited

U.S. PATENT DOCUMENTS

| 4,417,861 | A | * | 11/1983 | Tolbert ........................ 417/315 |
| 5,494,822 | A | | 2/1996 | Sadri |
| 7,011,623 | B2 | | 3/2006 | Clerin et al. |
| 7,611,830 | B2 | | 11/2009 | Thatte et al. |
| 2007/0202485 | A1 | * | 8/2007 | Nees et al. ..................... 435/1.1 |
| 2008/0027272 | A1 | | 1/2008 | Kadykowski |
| 2008/0208310 | A1 | * | 8/2008 | McDermott et al. ......... 623/1.11 |
| 2010/0331964 | A1 | | 12/2010 | Clerin et al. |

* cited by examiner

*Primary Examiner* — Catherine B Kuhlman
(74) *Attorney, Agent, or Firm* — Richard L. Strauss, Esq.

(57) ABSTRACT

Blood vessel preservation technology is disclosed wherein harvested blood vessels are attached to stationary attachment fixtures at one end, and to a non-stationary (freely extending) fixture at the other end. The vessel and fixtures are placed within a container. Thereafter, a stream of pulsatile blood is directed through the fixtures and the lumen of the vessel causing the vessel to assume full natural length and aligning the vessel with the container. The pulsatile blood then completely bathes the outside surface of the vessel before being re-circulated. The methods disclosed include those wherein the patient's own circulatory system is part of the circulatory path flowing through the vessel and methods in which the circulatory path is outside and apart from the patient. A pulsatile pump, blood heater and pressure regulator may all be utilized in preferred embodiments of the disclosed methods and devices.

20 Claims, 13 Drawing Sheets

METHOD AND DEVICE FOR PRESERVING THE VITALITY AND FUNCTION OF A HARVESTED BLOOD VESSEL

CONTINUITY DATA

This application is a continuation-in-part of U.S. patent application Ser. No. 11/653,528 filed Jan. 16, 2007 now U.S. Pat. No. 8,162,815, the entire content of which is hereby incorporated by reference into the present application.

TECHNICAL FIELD

The technology disclosed and claimed herein is most closely related to the science of blood vessel harvesting, preservation and grafting. More specifically, disclosed herein is a device and method for preserving an artery or vein, harvested for grafting, in a viable and functional state.

BACKGROUND OF THE INVENTION

Endothelial health and endothelial damage are major concerns in regard to coronary bypass grafts. This is especially true in regard to the late patency of such grafted vessels. To date, saline has been frequently utilized as preservative fluid for harvested vessels intended for use in bypass surgery. However, it is well known that saline produces significant endothelial damage in such vessels. It follows, as has been noted in various studies, that saline preserved grafts suffer significant impairment of vessel structure and function after anastomosis. In part, such degradation can be related to the absence of blood constituents which, in combination with the positive effects of natural blood flow, are required to maintain endothelial health.

The endothelial lining of arterial walls produces what was once known as endothelium-derived relaxing factor (which has since been identified as nitric oxide). Nitric oxide is, in turn, required in order for acetylcholine to effect relaxation of arterial smooth muscle—and to avoid damaging vessel spasms/contractions often noted in excised grafts—. NO, derived from the endothelium has further vessel patency functions beyond muscle relaxation. It is known to protect the vessel by inhibiting platelet and neutrophil adhesion to the endothelial walls as well as the arrest of smooth muscle cell proliferation. Based on the two aforementioned functions of NO, it follows that, in regard to maintaining patency of grafted vessels, preservation of the endothelium's natural production and release of NO is of extreme importance.

While, as discussed above, it is known that saline is a rather poor solution for use in preserving arterial grafts, blood is an excellent preservative. However, due to the fact that the normal constituents of blood (platelets, fibrin, leukocytes) as well as plasma components (such as cholesterol and triglycerides), negatively interact and damage endothelium during the harvesting/handling procedures, the simple infusion of blood into a harvested vessel would, of course, include additional draw backs. These interactions, of course, constitute an additional concern in regard to vessel patency. The aforementioned interactions of blood and plasma constituents with the endothelial lining are exacerbated in regard to blood which is allowed to pool. However, blood flowing through a vessel, as it does in its natural, pre-excised demonstrates greatly diminished interactions between the above-described blood/plasma constituents and the endothelial wall. More specifically, there is a substantially higher degree of interaction between blood/plasma components and the endothelial lining of vessels in stagnant blood, allowed to simply pool in an excised vessel, as opposed to the degree of interaction found in vessels conducting pulsatile, flowing blood.

In regard to blood flow and its effect upon harvested vessels beyond the aforementioned constituent/endothelial interactions, it is well known that application of a pulsatile flow to preservative solutions will improve and help maintain vessel dilatation. Pulsatile solution flow is also known to improve, nitric oxide production and release. In addition, flow pulsatility is known to reduce harvested vessel spasm. More specifically, harvested vessels, "acclimated" or conditioned to pulsatility—prior to being placed into arterial circulation—have increased likelihood of maintaining post-graft viability.

In addition to preservative fluid composition and pusatile blood flow, the temperature of storage and/or preservative solutions utilized to maintain harvested vessel vitality is of great significance. More specifically, as fluid temperature decreases below normal body temperature, loss of endothelium increases. Fluid temperatures beyond normal body temperature can also be quite damaging. It would therefore seem that a superior preservative technique, especially useful for the preservation of harvested blood vessels, would include the use of solutions maintained at normal body temperature.

Harvested vessels are also highly susceptible to damage caused by exposure to improper pH. For example, the relative acidic nature of normal saline is known to have detrimental effects on the endothelium. Also, hypoxic conditions which effect harvested vessels removed from active circulation can also cause enough damage as to substantially reduce graft survival. In addition, maintaining the natural patency of the lumen of harvested vessels, once removed from circulation, constitutes a problem. While over distension of such vessel due to the application of excess fluid pressure is highly damaging the endothelium, prolonged collapse of the lumen, and the associated hemolysis and clotting which may be caused thereby must also be avoided.

Blood is a superior preserving solution (as compared to saline). However, to date, a method and device have not been disclosed wherein blood, utilized as a preservative for harvested vessels, might be effectively and efficiently directed through the lumen of harvested arteries and veins while, at the same time, maintaining a temperature close to that of normal body temperature and a flow mimicking the pulsatile flow and pressure ranges to which the vessel is normally exposed (pre-excision) while, at the same time enabling a harvested vessel to extend to its normal, pre-excision length.

SUMMARY OF THE INVENTION

Now in accordance with the present invention, a method of blood vessel preservation is disclosed, especially designed, configured and adapted to preserve the viability of harvested blood vessels. The blood vessel method preservation of the present invention maintains and preserves the viability of harvested vessels for a period of time sufficient to allow anastomosis sites to be properly accessed and prepared prior to grafting of the harvested vessel into said site. More specifically:

The method of present invention comprises initially harvesting a blood vessel having a length, a proximal terminus, a distal terminus, a lumen, and an outer surface. Thereafter, the proximal terminus of the harvested vessel is attached to a stationary attachment fixture having a length, a proximal end, a distal end and a central bore running the entire length thereof. The central bore of the stationary fixture is continuous with and in fluid communication with openings located at the proximal and distal ends thereof so that when the proximal terminus of the harvested vessel is attached to the stationary fixture, the lumen of the vessel is placed in fluid communication with the distal opening, central bore and proximal opening of the fixture.

In practicing the method of the present invention, the distal terminus of the harvested vessel is attached to a non-stationary fixture having a length, a proximal end, a distal end, and a central bore. The central bore of the non-stationary fixture is continuous with and in fluid communication with openings located at the proximal and distal ends thereof so that when the distal terminus of the harvested vessel is attached to the non-stationary fixture, the lumen of the vessel is caused to be in fluid communication with the proximal opening, central bore and distal opening of the non-stationary fixture.

The method of the present invention further comprises introducing the non-stationary fixture, harvested vessel and stationary fixture into a central bore of a container having a length, a central bore running the length of the container, a proximal terminus and a distal terminus. The proximal terminus of the container is open and in fluid communication with the central bore of the container. The distal terminus is closed so as to form a fluid tight seal in regard to the central bore of the container. In practicing the method of the present invention, the stationary attachment fixture is secured to the proximal end of the container so as to fix the position of the proximal terminus of the blood vessel affixed thereto. In contrast, the non-stationary fixture is freely placed within the central bore of the container in such a manner as to enable the non-stationary fixture and the distal terminus of the vessel attached thereto, to move and freely extend along the length of the central bore of the container. The method of the present invention requires that the proximal terminus of the container is sealed so as to form a fluid tight seal for the central bore of the container except for: 1. a fluid conduit running from outside of the container through the proximal opening, central bore and distal of the stationary attachment fixture to the lumen of the blood vessel which, in turn, is in fluid communication with the central bore of the cannister by means of the proximal opening, central bore and distal opening of the non-stationary attachment fixture; and 2. a conduit provided by an outlet fitting located at the proximal end of the container providing fluid communication from outside of the cannister to the central bore of the vessel container.

In practicing the method of the present invention, a fluid stream of pulsatile blood is conducted through the opening located at the proximal end of the stationary attachment fixture so as to cause the fluid stream to flow through the conduit formed by the central bore of the stationary attachment fixture, the distal opening thereof and then through the lumen of the blood vessel. Thereafter, the pulsatile stream of blood is directed through the conduit formed by the proximal opening, bore and distal opening of the non-stationary attachment fixture. The pulsatile stream of blood then is pumped into, so as to fill the central bore of the container thereby, at the same time, completely bathing the outside surface of the blood vessel. Thereafter, the pulsatile stream of blood is conducted outside of the container by means of the container therein before exiting the outlet fitting. Thereafter, blood flowing out of the outlet fitting is directed via a fluid circuit which included, in the preferred embodiment, a pulsatile pump, back through the stationary fixture to form a complete fluid circuit. In addition, the method of the present invention contemplates directing the pulsatile flow of blood though a blood warmer and/or blood pressure regulator as discussed in more detail, below. Furthermore, the source of the pulsatile blood may be the patient's own circulatory system which, in certain preferred embodiments of the present invention, comprises part of the harvested vessel circulation. In other preferred embodiments of the present invention, the pulsatile flow of blood is separate and apart from the patient's circulation and may optionally include a blood reservoir for holding a sufficient volume of blood for circulation through the harvested vessel.

In practicing the method of the present invention, when the pulsatile flow of blood is pumped through the lumen of the blood vessel, it fills same and causes the blood vessel to extend to full natural length. The non-stationary attachment fixture aids such extension in enabling the vessel to freely extend while, in addition assisting alignment of the vessel (as discussed in more detail, below.)

In practicing the method of the present invention, a harvested blood vessel having a proximal and distal end, is affixed, at one end only, to a stationary and fixed point. In contrast, the opposite end of the vessel is left to freely move and extend. Although certain preferred embodiments of the present invention affix the proximal end of a harvested vessel to a "stationary attachment fixture"; so as to fix this terminus in a set position, the methods of the present invention also contemplate embodiments wherein the distal terminus of a harvested vessel is affixed to the stationary attachment point and the proximal terminus affixed to a non-stationary attachment point.

In practicing the methods of the present invention, after a pulsatile stream of blood is directed so as to flow through the lumen of the harvested blood vessel at the end thereof which is affixed in a stationary position the pulsatile blood completely fills and is conducted through the lumen of the harvested vessel so as to extend the blood vessel to its full length. Thereafter, the blood is further circulated, so as to flow out from the distal end of the blood vessel and through the non-stationary attachment fixture so as to flow over and bathe the entire outside surface of the blood vessel. Thereafter, the pulsatile flow of blood is circulated back through the harvested vessel.

In practicing the method of the present invention, it is required that one end of the blood vessel be affixed to a stationary position and the opposite end of the vessel be affixed in such a way as to enable that end of the vessel to freely extend and provide longitudinal alignment of the vessel—to enable the vessel to form a straight conduit—By affixing one end of the vessel to such a stationary point and affixing the opposite end of the vessel to an attachment point that enables and facilitates extension and alignment of the vessel. Therefore, the force of a pulsatile flow of blood flowing through the lumen of the vessel (from the stationary to the free end thereof) is properly directed towards extending and aligning the harvested vessel. Longitudinal alignment of the harvested vessel is, as discussed in greater detail below, necessary in order to assure that the outer surface of the vessel is fully and completely bathed with circulating blood. In utilizing a freely moving attachment point for one end of the harvested vessel, the method of the present invention avoids thus use of fixed attachment points at both ends of the harvested vessel which would not enable pulsatile blood to extend the vessel to its full length. In some instances, affixing a harvested blood vessel to fixed attachment points at both ends could over-extend the vessel. Conversely, utilizing such fixed attachment points could prevent the vessel from forming a straight conduit if the distance between the attachment points were less than the length of the vessel. Also, in such instances, such insufficient distance between the attachment points could cause the vessel to include folds, curves, or lie against a container in such a manner as to prevent complete bathing of the outer surfaces of the vessel with blood. Thus, utilizing a freely extending and aligning attachment point at one end of a harvested vessel prevents over-extension of the vessel, while enabling proper alignment and extension thereof to its natural length. The term "full length" and "full natural length" as utilized throughout this application and within the claims refers to the length of a harvested vessel as found in its natural state within the host and as attained when the lumen of the vessel is filled with a pulsatile flow of blood. In contrast, harvested blood vessels my assume less than their full natural length when they are removed from circulation and placed in a stagnant state where the lumen is allowed to collapse and the vessel is allowed to loose a portion of its natural fluid content. In addition, certain apparatus of the prior art mount harvested vessel at their proximal and distal ends to fixed positions. Such mounting may cause stretching of the vessel so that it assumes an unnaturally greater length. The methods of the present invention utilize a freely moving non-stationary attachment point at the distal end of a harvested vessel so that, by filling the vessel with a pulsatile stream of blood at the pressure ranges stated herein, the vessel assumes its normal—as found within the host before excision-length—its "natural full length.". It is also required, in practicing the method of the present invention, that blood exiting the freely moveable end of the blood vessel be directed, so as to completely bathe, the outside surface of the vessel to be preserved. For this purpose, it is essential for the blood vessel to be placed in a container capable of capturing blood which passes out the freely moving end of the vessel and further enable the blood to actively flow over the outer surface of the vessel before being re-circulated through the vessel. For this reason, as stated above, the methods of the present invention do not attach one end of the harvested blood vessel to a stationary point (or fixture) so as to enable the vessel to freely move and extend to full length and to form a relatively straight conduit. In practicing preferred methods of the present invention, a non-stationary attachment fixture is affixed to the harvested vessel at one terminus to both facilitate such extension and also so as to align the vessel in the center of a container so as to further facilitate complete bathing of the outside surface of the vessel with circulating blood. For example, in those embodiments of the methods of the present invention wherein an alignment fitting is utilized as the non-stationary fixture and is inserted in one terminus of the harvested vessel, the alignment fitting caused the longitudinal axis of the vessel to substantially align with the longitudinal axis of the container the vessel is placed within. Such alignment facilitates exposure to all portions of the outside surface of the vessel to be exposed to and bathed by the circulating blood. Without such facilitation, it is possible that the vessel might lie against an inner wall of a vessel container and thus prevent complete bathing of all outside surfaces thereof.

As discussed above and below, in certain integrated embodiments of the methods and devices of the present invention, the pulsatile flow of blood is provided from the donor's own circulatory system. In such embodiments, the blood directed through the harvested vessel is derived from the patient and returns to the patients' circulation after passing through and about the harvested vessel. In such instances, the pulsatile flow provided by the patient's own heart may optionally be assisted by a mechanical pulsatile pump. However, in non-integrated embodiments of the present invention wherein the preservation system is autonomous and depends entirely upon a mechanical pump (pulsatile pump) for blood flow, it is highly advantageous to warm, oxygenate and add nitric oxide to the circulating blood to increase blood vessel viability.

U.S. patent application Ser. No. 11/653,528 discloses some of the devices that are especially well adapted for practicing the methods of the present invention. The blood vessel preservation device disclosed in the Ser. No. 11/653,528 application (the "528 application") is comprised of a vessel cannister, cannister cap, vessel alignment insert, pulsatile pump and both inlet and outlet tubing. The vessel canister is advantageously configured as a hollow tube-like structure with a central bore having one open terminus—the proximal terminus—and a closed distal terminus—similar to a large test tube—. It may, for example, be advantageously fabricated from a medical grade glass. The canister may also be advantageously fabricated from a medical grade plastic polymer such as, for example, acetal, polysulfone, polyphenylsulfone, polythermide, UHMW, polycarbonate, acrylic, polypropylene, PTFE and antimicrobial filled polymers. It is highly advantageous to utilize a transparent polymer for fabrication of the canister so as to enable gross visual observation of a vessel contained therein as discussed in more detail, below. The vessel cannister, as discussed in more detail below, enables one, practicing the method of the present invention, to flow blood over, so as to bathe, the entire outside surface of a harvested vessel prior to recirculating the blood through the vessel.

The cannister cap of the '528 application may be described as including a top portion configured in a flattened circular shape with side wall portions extending therefrom. During application of the cannister cap to a vessel canister, it is the top portion of the cannister cap that actually occludes the proximal opening of the vessel cannister The side walls of the cap, extending at approximately 90 degrees from the top portion, circumferentially engage the vessel cannister—either on the outside surface or inside surface therein—adjacent the proximal terminus thereof so as to maintain the cap upon the cannister with a fluid tight seal—except for ports formed by the attachment fitting and outlet fitting, discussed in more detail, below. As mentioned above, the side wall portion of the cannister cap is advantageously shaped and configured so that the inner or outer surfaces thereof mate with and form a seal with the vessel cannister adjacent to the proximal terminus thereof.

The cannister cap of the '528 application also includes a vessel engagement fitting as well as a canister outlet fitting. The vessel engagement fitting provides—at the distal end thereof, the means of enabling one, practicing the method of the present invention, to affix one end of a harvested blood vessel to a stationary point. The cannister outlet fitting provides a means of recirculating blood that has cycled through and about a harvested vessel contained within the cannister to return to the source of pulsatile flow (pulsatile pump and/or heart) and thereafter return to the cannister to form a complete circulatory track.

The cannister cap may, for example, be advantageously formed from a medical grade glass material. It may be further advantageous to fabricate the cannister cap from a medical grade polymer such as, for example, acetal, polysulfone, polyphenylsulfone, polythermide, UHMW, polycarbonate, acrylic, polypropylene, PTFE and antimicrobial filled polymers.

The vessel engagement fitting disclosed in the '528 application, in the first preferred embodiment described therein, is mounted, eccentrically, within the top portion of the cannister cap as a contiguous structure thereof. The engagement fitting includes an opening at both the proximal and distal terminus thereof. The openings of the proximal and distal terminus of the engagement fitting are in fluid communication with a central bore running, axially, along the full length of the engagement fitting so as to form a conduit. When the cannister cap is matingly engaged with the vessel canister at the proximal terminus of the cannister, the distal portion of the vessel engagement fitting is contained within the vessel container and, in preferred embodiments, is axially aligned with the center of the central bore of the cannister. The outer surface of the engagement fitting, adjacent to the distal terminus thereof, may advantageously include circumferential ribs so as to, as described in more detail below, enhance engagement of the proximal portions (lumen) of harvested vessels. Thus, in regard to the device disclosed and claimed within the '528 application, the distal portion of the vessel engagement fitting provides the means of affixing the harvested blood vessel in a stationary position and also provides the means of directing a flow of blood (by providing a conduit) through the lumen of a harvested vessel mounted upon the engagement fitting.

In the first preferred embodiment disclosed within the '528 application, the proximal terminus of the vessel engagement fitting extends obliquely outward and eccentrically from the top surface of the cannister cap. The outer surface of the proximal portion of the vessel engagement fitting is especially sized and configured to enable engagement of a blood inlet tube, discussed in detail, below. In certain embodiments of the present invention, this outer surface may also include circumferential ribs so as to better engage and maintain surgical tubing attached thereupon. The blood inlet tube and the blood vessel engagement fitting disclosed in the '528 application thus provide the means of introducing a pulsatile flow of blood through a harvested vessel mounted upon the distal end of the engagement fitting.

The canister cap of the device disclosed in the '528 application is adapted to matingly engage the vessel container. The proximal terminus of the engagement fitting extends outside of the cannister/cap. The distal terminus of the engagement fitting lies within and, in preferred embodiments of the present invention, is aligned with the central axis of the central bore of the cannister. The central bore of the engagement fitting, runs from the distal to proximal terminus thereof and communicates with the openings located at both such termini providing a conduit—a fluid communication—between the lumen of a vessel mounted thereupon and, via the opening at the proximal terminus of the vessel engagement fitting, outside of the cannister (and to any tubing attached to the proximal terminus of the fitting).

The device disclosed and claimed in the '528 application also includes a cannister outlet fitting—which in preferred embodiments may also be formed as a contiguous part of the cannister cap—but, in all cases, is most advantageously positioned adjacent to the proximal end of the container. The cannister outlet fitting is disclosed so as to include a central bore, as well as proximal and distal terminus (both defining opening). The outlet fitting is also disclosed as center mounted upon the top portion of the cannister cap. The distal terminus of the outlet fitting defines an opening which, in certain preferred embodiments of the present invention, is within and continuous with the inner surface of the top portion of the cannister cap. When the cannister cap is engaged to the proximal portion of the cannister, then the distal opening of the outlet fitting is open to and in fluid communication with the central bore of the vessel cannister. The proximal terminus, as described above, includes an opening which is in fluid communication with the central bore of the outlet fitting. Thus, a conduit is formed which runs from the opening at the proximal terminus of the outlet fitting, through the central bore of the outlet fitting and through the opening located at the distal terminus thereof. Thus, the proximal opening of the outlet fitting is open and in fluid communication with the central bore of the vessel cannister when the cap has engaged the vessel cannister. Thus, the cannister outlet fitting enables, in conjunction with the central bore of the vessel cannister, circulation of a pulsatile flow of blood that bathes the outside surface of a harvested vessel contained within the cannister and then exits the cannister via the outlet fitting so as to re-circulate.

The vessel alignment insert disclosed in the '528 application may be described as including a disc-like portion located at the distal part thereof, and a tube-like portion extending proximally therefrom. The disc-like portion may be configured, for example, to demonstrate a diameter slightly less than that of the central bore of the cannister so that, as described below, the disc helps extend and align a harvested vessel when the vessel is infused with blood. In preferred embodiments of the present invention, the disc-like portion includes a plurality of perforations therein, at least one of which is aligned with a central bore penetrating the disc-like portion of the insert and thence running the entire length of the tube-like portion of the vessel alignment insert and communicating with the proximal opening located at the proximal terminus of the tube-like portion. The proximal terminus of the tube-like portion is especially configured and adapted to enable secure insertion thereof into one end of the harvested vessel. In certain preferred embodiments of the present invention, the outer surface of the tube-like portion of the insert, adjacent to the proximal terminus thereof, is especially configured to include circumferential ribs so as to facilitate engagement of the lumen of harvested vessels proximal to the distal portions thereof. Thus, as mentioned above, the distal terminus of the tube-like portion of the vessel alignment insert includes an opening aligned with and continuous with the central bore of the tube-like portion which, in turn, is aligned with and continuous with the at least one of the perforations of the disc-like portion of the insert. Therefore, when inserted into the lumen of a blood vessel, the alignment insert provides fluid communication running from the lumen of the vessel, through the proximal terminus of the tube like portion of the insert, through the central bore thereof, and through at least one perforation of the disc-like portion of the insert and into the central bore of the vessel cannister. Thus, blood flowing within the harvested vessel, as discussed below, is able to exit the vessel, via the proximal opening of the alignment insert, through the bore thereof, and out the at least one perforation leading to the central bore of the cannister. The alignment insert of disclosed in the '598 application enables, in accordance with the methods of the present invention, enabling one end of the harvested vessel to freely move and extend (via a non-stationary attachment fixture), while also facilitating the vessel's alignment with the longitudinal axis of the vessel cannister. The free extension of the harvested vessel to its natural length provided by the present method does not overextend the vessel as might occur with methods and devices that insert both termini of a harvested vessel into stationary fittings/fixtures. In addition to promoting the extension and alignment of a harvested vessel, the vessel alignment insert described within the '528 application also has a protective function in that the insert prevents the distal end of the vessel from flailing about a vessel container (e.g., vessel cannister) which such thrashing about might otherwise cause damage to the vessel. Thus, when a pulsatile stream of blood is directed through the harvested vessel in accordance with the methods described herein, the non-stationary fixture which is affixed to the distal end of the vessel: 1. enables the vessel to reach the same length it would attain in natural circulation when blood flowing therethrough—within the range of normal blood pressures—; 2. causes the vessel to align with the longitudinal axis of the vessel cannister within which it is contained; and 3. protects the vessel from flailing about the container in which it is placed so as to avoid injures contact therewith.

The vessel alignment insert disclosed in the '528 application may be advantageously fabricated from a medical grade glass. However, it is still further advantageous to fabricate the insert from a medical grade plastic polymer such as, for example, acetyl, polysulfone, polyphenylsulfone, polythermide, UHMW, polycarbonate, acrylic, polypropylene, PTFE and antimicrobial filled polymers. As stated in regard to the vessel cannister and cannister cap, it is advantageous that the vessel insert be fabricated from a transparent material.

In embodiments wherein the method of the present invention is utilized separately and apart from the circulatory system of the patient (non-integrated embodiments), the method requires that an artificial source of pulsatile blood flow be provided. The device disclosed in the '528 application utilizes a pulsatile pump for such embodiments so as to provide the pulsatile flow of blood—required by the method of the present invention—through a harvested vessel contained within the vessel cannister (as described in more detail, below. This pulsatile flow of the present invention tends to enhance the viability of a harvested vessel contained within the device. Ventricular-type pneumatic or hydraulic pumps (e.g., Keele pump, Polystan pulsatile pump), modified roller pumps (e.g., Sarns and Stockert), and modified centrifugal pumps (e.g., Sarns) may be advantageously selected as pulsatile pumps for use in the device of the present invention. In addition, roller pumps, and especially pulsatile roller pumps may be utilized. Regardless of the pumps utilized, the flow of the pump is adjusted so as to provided a pulse pressure of from about 60 to 150 mmHg. Within this pressure range, sufficient pressure is provided so as to maintain an open and patent harvested vessel lumen without danger of the damage caused by over distension thereof. Also, such pressure ranges assure that, when blood is pumped through the harvested vessel, the free end thereof—the end affixed to a non-stationary fixture (or attachment point) will cause the vessel to extend to its natural full length. In the absence of a pulsatile flow of blood coursing through the lumen of a harvested vessel, the length of the vessel may be reduced due to the drop in internal lumen pressure as contrasted with the natural pressure ranges found within the lumen while the vessel remains in natural circulation within the patient. In maintaining a pressure range of from about 60 to about 150 mmHG, the method of the present invention also avoids coursing a Significantly higher lumen pressure which might cause both damage to the tissues lining the lumen as well as lead to an un-natural over-extension of the vessel's length. Thus, the device of the present invention requires either a pressure regulated pump (a pump including an integral and adjustable pressure regulator), a separate pressure control device, or the use of both a variable output (pressure) pump and pressure control device. In practicing methods of the present invention wherein the harvested vessel remains connected with the circulatory system of a patient, the patient's own heart provides the required natural range of pulsatile blood flow pressure.

Similarly, in certain preferred embodiments of the present method, wherein pulsatile blood is circulated through a harvested vessel separate and apart from a patients circulatory system, the method may be enabled by utilizing a blood warming device wherein blood circulates therethrough. As discussed in the '528 application, blood warmers such as the "Fluido" device (Fluido b.v., The Surgical Company) are especially useful in that they combine both accurate temperature control and monitoring functions The method of the present invention provides a means of enhancing and prolonging the viability of a harvested vessel by means of utilizing devices, such as those disclosed within the '528 application. The method of the present invention, and the devices utilized in practicing same, are most advantageously utilized immediately after a harvested blood vessel has been removed from a patient.

By way of example, in practicing the method of the present invention utilizing the devices disclosed and claimed in the '528 application, initially, the distal end of the harvested vein (or artery) is clamped off. Thereafter, blood is forced into the lumen of the vessel at the proximal (and open) end of the vessel via manual syringe instillation. Manual infusion of blood into the harvested vessel is performed in order to identify any side branches not already tied off or clamped during the harvesting procedure. Any such side branches so identified (via the extravasation of blood) are quickly tide off, clamped or otherwise occluded in the usual manner.

Once the harvested vessel has been tested for side branches—and any identified side branches occluded—, the aforementioned clamp and syringe are removed therefrom. Thereafter, the proximal end of the tube-like portion of the vessel alignment insert—a moveable attachment point—is inserted into the lumen of the harvested vessel at the distal end of said vessel. The distal terminus of the vessel engagement fitting—a fixed attachment point—is then inserted within the lumen of the harvested vessel at the proximal terminus of said vessel. Thereafter, the vessel alignment insert is inserted into the bore of the vessel cannister, with the disc-like portion of the alignment insert being introduced first. Thereafter, the harvested vessel is introduced into the cannister and the cannister cap, now engaging the lumen of the harvested graft (adjacent the proximal terminus), is mated and engages the canister adjacent to the open proximal terminus thereof to form a fluid tight seal (other than the conduit provided by the bore of the engagement and outlet fittings).

The method of the present invention may be advantageously operated with—in preferred (integrated) embodiments—, blood circulating from and returning to the patient undergoing the harvesting/graft procedure. The patients own naturally heated and oxygenated blood therefore serves as the preserving fluid for the harvested vessel. Therefore, for example, a catheter inserted into the patient's femoral artery may be utilized to supply blood. In certain embodiments of such integrated methods, the blood supplied from the femoral artery is conducted, via the usual surgical tubing, to the inflow side of a pusatile pump used in accordance with the device and method of the present invention so as to enhance the flow of blood. The pulsatile pump, as discussed above, maintains natural flow pulsatility which, in turn, provides improved harvested vessel dilatation, nitric oxide production and reduction in vessel spasm. Thereafter, additional surgical tubing is utilized to connect the outflow of the pulsatile pump to the proximal end of the vessel engagement fitting.

As discussed above, in regard to practicing the method of the present invention with the device disclosed within the '528 application, the opening at the proximal end of the vessel engagement fitting is in fluid connection with the central bore running the entire length of the engagement fitting, the opening at the distal end of the fitting and, of course, with the lumen of the harvested vessel now engaged by the fitting. Blood flowing from, for example, the femoral artery, thus travels through surgical tubing (which is utilized as a conduit). In practicing certain preferred embodiments of the present invention, even though blood is derived from the patient's own circulatory system, a pulsatile pump is utilized to enhance circulatory flow. Whether or not such pulsatile pumps are utilized, blood flowing from the patient is directed via surgical tubing through, in regard to the devices disclosed in the '528 application, the vessel engagement fitting and on through the harvested vessel to the distal terminus thereof. Thereafter, blood passes through the opening located at the proximal end of the vessel alignment fitting, through the bore thereof and out the at least one perforation located on the disc-like portion of the fitting aligned with said bore. As the blood fills the lumen of the vessel contained within the cannister, the pressure caused thereby, in conjunction with the aligning action of the vessel insert, causes the vessel to extend along the length of the vessel cannister to its full length. Thereafter, the blood fills the remaining central bore of the canister until it reaches the cannister outflow fitting located within the cannister cap. Thus, the '528 device provides complete bathing of the outside surface of the harvested blood vessel via circulating blood. Blood which has filled the cannister and reached the outflow fitting thence passes through the opening located at the distal end of the fitting, passes through the bore thereof, and out the proximal opening of the fitting. Additional surgical tube, connecting the outflow fitting of the cannister cap, is utilized to provide return of blood circulated through the device and vessel maintained therein to a vein within the patient's circulation. The methods of the present invention can optionally include regulation of the pressure of the pulsatile blood circulated through a harvested vessel. As mentioned above, such methods require a device be utilized which includes either a pressure regulator integral to pulsatile pump (for those embodiments utilizing such pumps), or a separate pressure regulator. to maintain pressure entering the harvested vessel from about 50 to about 150 mmHG. However, regardless as to device configuration, autonomous circulation or integral methods wherein the harvested vessel remains in circulatory connection with the patient, it is highly desired to maintain pressure of the pulsatile blood flow entering the harvested vessel at said 50 to about 150 mmHg. pressure.

The above-described embodiment of the present invention may be described as an integrated blood flow embodiment of the method of the present invention. However, the present invention also contemplates embodiments thereof, wherein, after sufficient blood has been collected from the patient's circulation (as described above, the blood is continually circulated within the flow circuits of the device without return to the patient's own circulatory system. Such embodiments may also advantageously utilize a blood heating device so as to maintain the temperature of the blood substantially equal to normal body temperature. The above-described integrated embodiments wherein blood continuously flows from patient to device (and harvested vessel) and back to the patient obtain the heat required to maintain blood flowing through the harvested vessel at near normal body temperature from the patient's own body. It should be noted however, even such embodiments may be supplemented with the additional step of heating the blood via an external blood heating device.) However, non-integrated embodiments of the present invention which do not remain connected to a patient's circulation after initial "filling" of the system will continuously lose heat without the aforementioned additional heating device. Such non-integrated embodiments of the present method require the additional step of heating the blood circulating through the harvested vessel. Such devices, as disclosed within the '528 application, enable maintenance of blood temperature at about 40° C. and, of course, have overheat controls preventing blood from heating beyond 43° C. Blood warmers such as the "Fluido" device (Fluido b.v., The Surgical Company) are especially useful in that they combine both accurate temperature control and monitoring functions. In addition, such non-integrated embodiments may also utilize a reservoir in order to collect sufficient blood from a patient and thereafter make sufficient blood available for circulation through the vessel.

DETAILED DESCRIPTION

Figure 1:
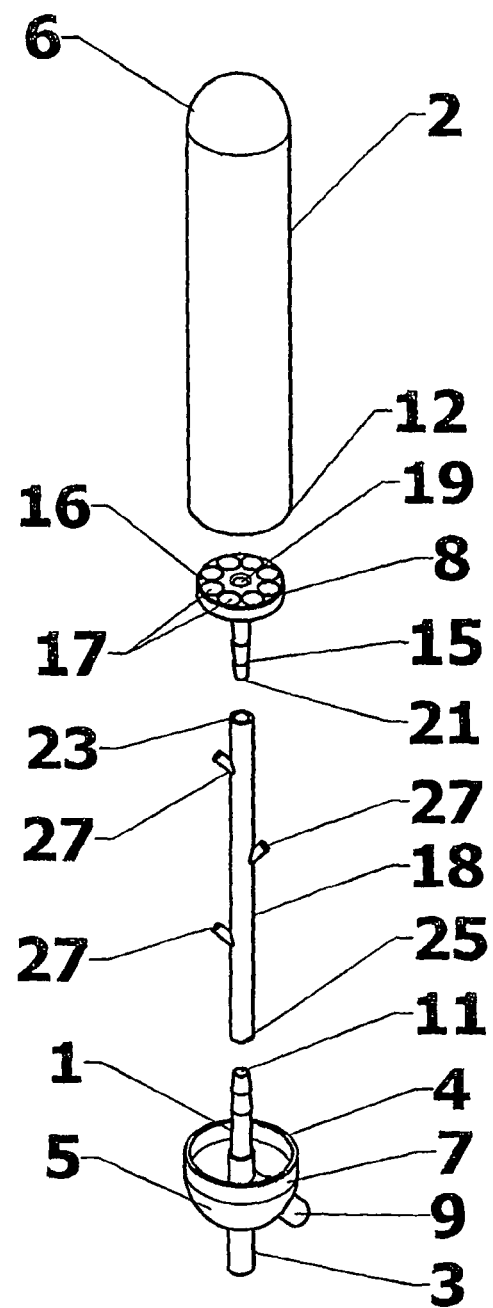
FIG. 1 illustrates an exploded view of a preferred vessel cannister, cannister cap and vessel alignment insert utilized in the device and method of the present invention.

FIGS. 1-4 illustrate a blood vessel preservation device disclosed within the '528 application and especially configured and adapted to practice the method of the present invention. Although the design and configuration of this illustrated device are well adapted to practicing the methods of the present invention, FIGS. 5-9, discussed below, illustrate further devices also well suited to such methods.

The devices illustrated in FIGS. 1-5 are comprised of a vessel cannister 2, cannister cap 4, vessel alignment insert 8, pulsatile pump 24, and both inlet 30 outlet 20 tubing. As illustrated in greater detail within FIG. 1, the vessel canister 2 is advantageously configured as a hollow tube-like structure with a central bore having one open terminus—the proximal terminus 12—and a closed distal terminus 6. The canister may be advantageously fabricated from a medical grade glass. The canister may also be advantageously fabricated from a medical grade plastic polymer such as, for example, acetal, polysulfone, polyphenylsulfone, polythermide, UHMW, polycarbonate, acrylic, polypropylene, PTFE and antimicrobial filled polymers. It is highly advantageous to utilize a transparent medical grade plastic for fabrication of the cannister so as to enable gross visual observation of a vessel contained therein (as would, of course, also be provided by transparent, medical grade glass).

As illustrated in FIG. 1, the cannister cap 4 is comprised of a top portion 5 shaped and configured, for example, as a circular dome-like structure having side walls 7 extending therefrom. During application of the cannister cap to a vessel canister, it is the top portion of the cannister cap that actually occludes the proximal opening of the vessel cannister while the side walls of the cap, extending at approximately 90 degrees from the top portion, engage the vessel cannister circumferentially adjacent the proximal terminus thereof so as to maintain the cap upon the cannister with a fluid tight seal. The side wall portion of the cannister cap may be advantageously shaped and configured so that either the inner or outer surfaces thereof mate with and form a fluid seal with the vessel cannister adjacent to the proximal terminus of the cannister. The cannister cap includes a vessel engagement fitting 1 as well as a canister outlet fitting 3 which are described in more detail both above and below. The cannister cap may be advantageously formed of a medical grade glass material. It is further advantageous to fabricate the cannister cap from a medical grade polymer such as, for example, acetal, polysulfone, polyphenylsulfone, polythermide, UHMW, polycarbonate, acrylic, polypropylene, PTFE and antimicrobial filled polymers.

The cannister cap may be formed and configured so that the vessel engagement fitting 1, is mounted, for example, eccentrically, within the top portion of the cannister cap and as a contiguous structure thereof. However, eccentric mounting is not required. Therefore, in some embodiments, the engagement fitting may be in centric alignment. The engagement fitting includes a central bore and has an opening at both the proximal 9 and distal 11 terminus thereof. The openings of the proximal and distal terminus of the engagement fitting are in fluid communication with the central bore running, axially, along the full length of the engagement fitting. When the cannister cap is matingly engaged with the vessel canister at the proximal terminus of the cannister, the distal portion of the vessel engagement fitting is contained within the vessel container and, in preferred embodiments, is axially aligned with the center of the central bore of the cannister. It is highly advantageous to so axially align the distal portion of the engagement fitting which extends from below the top portion of the cap. More specifically, such a configuration enables that portion of a harvested vessel mounted thereupon to be aligned with the diametric center of the cannister. This positioning, in combination with the alignment fitting discussed above and below, cause the vessel to extend along and align with the diametric center (longitudinal alignment) of the vessel cannister. This alignment, in turn, assures the vessel is properly extended in a straight configuration and also ensures that the outer surface of the vessel is completely and evenly exposed to the circulating, pulsatile flow of blood that bathes said surface when practicing the method of the present invention.

The outer surface of the engagement fitting disclosed in the '528 application, adjacent to the distal terminus thereof, may advantageously include circumferential ribs so as to provide, as described in more detail below, enhanced engagement of the proximal portion (lumen) of harvested vessels. In preferred embodiments of that device (as illustrated in FIG. 1), the proximal terminus of the vessel engagement fitting extends obliquely outward and eccentrically from the top surface of the cannister cap. The outer surface of the proximal portion of the vessel engagement fitting is especially sized and configured to enable engagement of a blood inlet tube, discussed in detail, below. In certain preferred embodiments of the device illustrated in FIG. 1, the outer surface of the vessel engagement fitting, adjacent to the proximal terminus thereof, may also include circumferential ribs so as to better engage and maintain surgical tubing attached thereupon.

As discussed above in regard to the device disclosed in the '528 application (FIG. 1), when the canister cap is matingly engaged about the proximal terminus of the vessel container, the proximal terminus of the engagement fitting extends obliquely outside of the cannister/cap and the distal terminus lies within and is aligned with the central axis of the central bore of the cannister. Thus, the central bore of the engagement fitting, running from the distal to proximal terminus thereof, and communicating with the openings located at both such termini, provides fluid communication between the central bore of the vessel container and the opening at the proximal terminus of the vessel engagement fitting (as well as any tubing attached thereto). This fluid communication is true whether or not a vessel is mounted upon the distal portion of the engagement fitting. In instances wherein a vessel is so engaged and mounted, the lumen of the vessel provides communication between the bore of the engagement fitting and the central bore of the vessel container.

The device illustrated in FIG. 1 includes a cannister outlet fitting 3 which may be formed as a contiguous part of the cannister cap. The cannister outlet fitting includes a central bore in fluid communication with openings formed at the proximal and distal terminus of the outlet fitting. In the embodiment illustrated in FIG. 1, the canister outlet fitting 3 is center mounted upon the top portion of the cannister cap. However, such center mounting is not required. As mentioned above, the distal terminus of the outlet fitting defines an opening within and continuous with the inner surface of the top portion of the cannister cap in the center thereof. Thus, the distal opening of the outlet fitting is open to and continuous with the central bore of the outlet fitting which is also continuous, and provides fluid communication with the proximal opening thereof. Thus the proximal terminus of the outlet fitting is open and in fluid communication with the central bore of the vessel cannister when the cap has engaged upon the vessel cannister.

The device illustrated in FIG. 1 and disclosed within the '528 application includes a vessel alignment insert 8 which includes a distal disc-like portion 16 and a tube-like portion 15 extending proximally therefrom. The disc-like portion 16 of the insert demonstrates a diameter slightly less than that of the central bore of the cannister so that, as described in more detail below, when blood is pumped through a harvested vessel mounted upon the insert, the disc helps extend and align a harvested vessel within the central bore of the cannister. The disc-like portion includes a plurality of perforations therein 17, at least one of which, preferably a central perforation 19, is aligned with and in fluid communication with a central bore running the length of the tube-like portion 15 of the vessel alignment insert and thus communicates with a proximal opening located at the proximal terminus 21 of the tube-like portion. All of the afore-mentioned perforations are also in fluid communication with the central bore of the vessel cannister. An outer surface of the tube-like portion of the insert, adjacent to the proximal terminus thereof, may advantageously include circumferential ribs so as to facilitate engagement of the lumen of harvested vessels at the distal portions thereof. As mentioned above, the proximal 21 terminus of the tube-like portion of the vessel alignment insert includes an opening aligned with and continuous with the central bore of the tube-like portion which, in turn, is aligned with and continuous with the at least one of the perforations— preferably a centrally positioned perforation 19—of the disc-like portion 16 of the insert. Therefore, there is fluid communication running from the proximal portion of the tube like portion of the insert, through the central bore thereof, and through at least one perforation of the disc-like portion of the insert. Thus, blood flowing through the lumen of a harvested vessel mounted upon the insert, as discussed below, is able to exit the vessel, via the proximal opening of the insert, through the bore, and out the at least one perforation leading to the central bore of the cannister. The vessel alignment insert is advantageously fabricated from a medical grade glass. However, it is still further advantageous to fabricate the insert from a medical grade plastic polymer such as, for example, acetal, polysulfone, polyphenylsulfone, polythermide, UHMW, polycarbonate, acrylic, polypropylene, PTFE and antimicrobial filled polymers. As stated in regard to the vessel cannister and cannister cap, it is advantageous that the vessel insert be fabricated from a transparent material.

Figure 2:
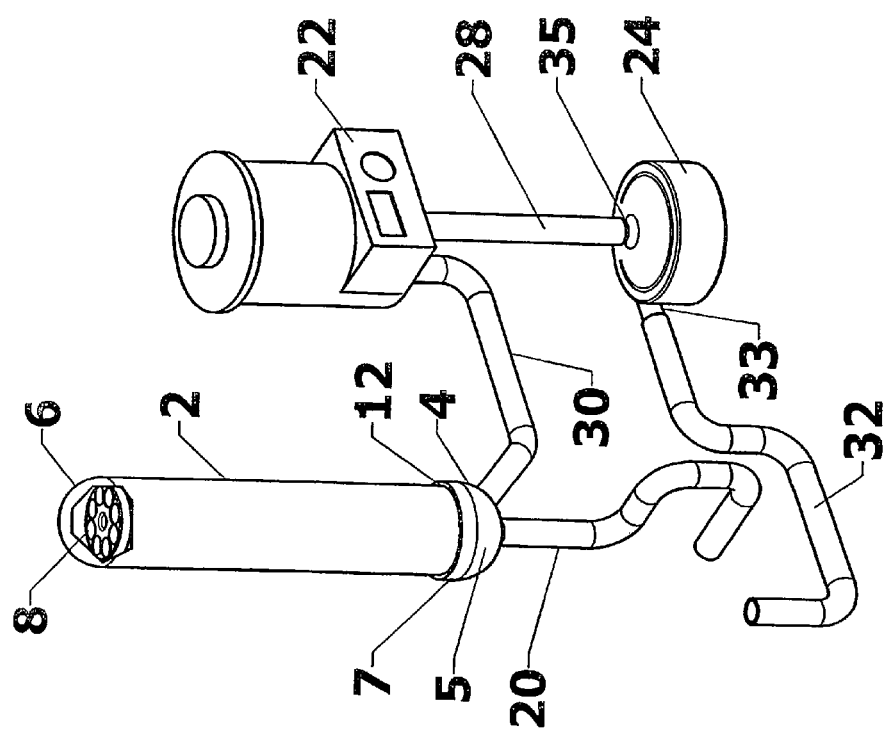
FIG. 2 is a front left view of the blood vessel preservation device of the present invention incorporating the vessel cannister, cannister cap and vessel alignment insert illustrated in FIG. 1.
Figure 3:
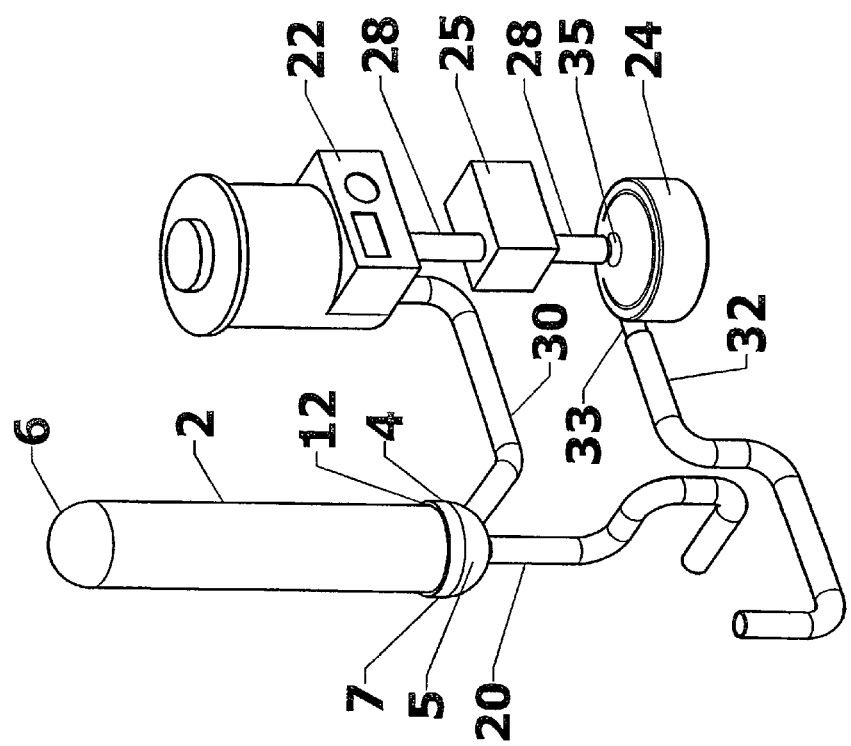
FIG. 3 is a front left view of a second preferred embodiment of the blood vessel preservation device of the present invention incorporating the vessel cannister, cannister cap and vessel alignment insert illustrated in FIG. 1.
Figure 4:
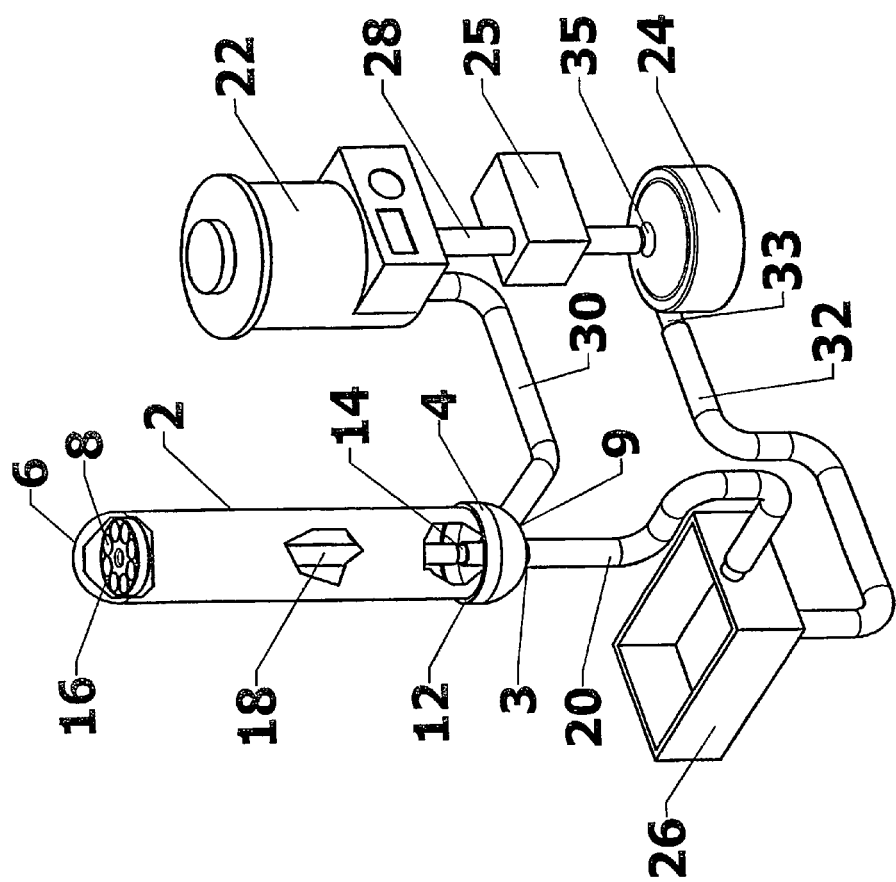
FIG. 4 is a front left view of a third preferred embodiment of the blood vessel preservation device of the present invention incorporating the vessel cannister, cannister cap and vessel alignment insert illustrated in FIG. 1.

FIGS. 2, 3 and 4 further illustrate a device especially configured and adapted to practice the method of the present invention. The device utilizes a pulsatile pump 24 so as to provide a pulsatile flow of blood through a harvested vessel contained within the vessel cannister (as described in more detail, below). The pulsatile pump provides such flow in the illustrated embodiment. However, as stated above, certain integrated embodiments of the method of the present invention utilize a patient's own circulatory system to provide the circulating blood as well as the pulsatile flow (via force provided by the patient's own heart). In such embodiments, a pulsatile pump may be optionally utilized within the circuit, but is not required in all instances.

As described above, pulsatile blood flow—whether derived from an external pump or the patient's own heart—tends to enhance the viability of a harvested vessel and thus also enhances the viability of vessels contained within the cannister through which pulsatile blood flow is provided. Ventricular-type pneumatic or hydraulic pumps (e.g., Keele pump, Polystan pulsatile pump), modified roller pumps (e.g., Sarns and Stockert), and modified centrifugal pumps (e.g., Sarns) may be advantageously selected as pulsatile pumps for use in the device of the present invention. In addition, roller pumps, and especially pulsatile roller pumps may be utilized. Regardless of the pumps utilized, the flow of the pump is adjusted so as to provided a pulse pressure of from about 60 to 150 mmHg. Within this pressure range, sufficient pressure is provided so as to maintain an open and patent harvested vessel lumen without danger of the damage caused by over distension thereof. To maintain pressure within this range, the device of the present invention requires either a pressure regulated pump (a pump including an integral and adjustable pressure regulator), a separate pressure control device 25 as illustrated in FIGS. 3 and 4, or the use of both a variable output (pressure) pump and pressure control device.

As stated above, in certain preferred embodiments of the present invention, wherein the method and devices configured to perform such method are utilized separate and apart from a patient's circulatory system, a pulsatile pump is required. In addition, the device may further include a means of warming blood circulating therethrough. Such devices are most often required since, as described above, harvested vessel viability is enhanced by providing blood temperature close to natural somatic levels. Blood warmers such as the "Fluido" device (Fluido b.v., The Surgical Company) are especially useful in that they combine both accurate temperature control and monitoring functions The method of the present invention provides a means of enhancing and prolonging the viability of a harvested vessel by means of utilizing a device of the present invention especially configured and adapted for practicing such methods. All such devices are advantageously utilized immediately after a harvested blood vessel has been removed from a patient.

In practicing the method of the present invention in regard to the device illustrated in FIGS. 1-5, initially, the distal end 23 of the harvested vein (or artery) 18 is clamped off. Thereafter, blood is infused into the lumen of the vessel at the proximal 25 (and open) end of the vessel via manual syringe instillation. Manual infusion of blood into the harvested vessel is performed in order to identify any side branches 27 not already tied off or clamped during the harvesting procedure. Any such side branches so identified (via the extravasation of blood) are quickly tide off, clamped or otherwise occluded.

Once the harvested vessel has been tested for side branches—and any identified side branches occluded—, the aforementioned clamp and syringe are removed therefrom. The distal end of the vessel engagement fitting 11 is inserted into the lumen of the harvested vessel at one end thereof. In most instances, it will be the proximal end 25 of the vessel which is so engaged. Such engagement of the lumen of the harvested vessel at one end by the vessel engagement fitting provides the stationary affixation of one end of the harvested vessel as required by the present method.

The proximal end 21 of the tube-like portion of the vessel alignment insert is inserted into the lumen of the harvested vessel at the opposite end 23 of the vessel (which is most often the distal end of said vessel). Such engagement enables, in accordance with the methods of the present invention, movement of one end of the harvested vessel as well as guided alignment and extension thereof. It also prevents the blood vessel from flailing about a vessel container thereby avoiding damage which might be caused by such contact.

Thereafter, the vessel alignment insert is inserted into the bore of the vessel cannister, with the disc-like portion of the alignment insert being introduced first. Insertion of the Thereafter, the harvested vessel is introduced into the cannister and the cannister cap, now engaging the lumen of the harvested graft (adjacent the proximal terminus), is mated and engages the canister adjacent to the open proximal terminus thereof. The engagement of the canister cap with the proximal terminus of the vessel canister enables formation of a chamber which allows bathing of the outside surface of the contained vessel in accordance with the methods of the present invention.

As mentioned above, the methods and devices of the present invention are advantageously operated with—in preferred embodiments—, blood circulating from and returning to the patient undergoing the harvesting/graft procedure. The patients own naturally heated and oxygenated blood therefore serves as the preserving fluid for the harvested vessel. Therefore, for example, a catheter inserted into the patient's femoral artery may be utilized to supply blood, via the usual surgical tubing 32, to the inflow side 33 of a pusatile pump 24 used in accordance with the device and method of the present invention. The pulsatile pump, as discussed above, maintains natural flow pulsatility which, in turn, provides improved harvested vessel dilatation, nitric oxide production and reduction in vessel spasm. However, in such instances of integrated embodiments, the pulsatile flow provided by the patient's own heart may be sufficient so as to obviate the need for such pulsatile pumps.

As shown in FIGS. 1-5, certain devices especially configured and adapted for practicing the methods of the present invention utilize additional surgical tubing to connect the outflow 35 of the pulsatile pump:

1. directly to the proximal end of the vessel engagement fitting 9;
2. to the input of a pressure regulation device 25 which, in turn, directs the blood, via its output side, directly to the vessel engagement fitting or,
3 in other preferred embodiments, directs blood flow to a blood warmer 22.

In embodiments of the present invention utilizing a blood warmer, outflow therefrom may be directed to the vessel engagement fitting.

As discussed above in regard to the devices illustrated in the figures, the opening at the proximal end of the vessel engagement fitting is in fluid connection with the central bore running the entire length of the engagement fitting, the opening at the distal end of the fitting and, of course, with the lumen of the harvested vessel engaged by the fitting. Blood flowing from, for example, the femoral artery, thus travels through the surgical tubing to the pulsatile pump, and thence via further tubing 28 either directly to the vessel engagement fitting and on through the harvested vessel to the distal terminus thereof. (In other preferred embodiments of the invention discussed above and below, blood outflowing from the pulsatile pump may first pass through an intermediary pressure regulator and, in certain preferred embodiments, a blood warmer prior to being directed to and through the vessel engagement fitting.)

As described above, after blood has passed through the lumen of the harvested vessel, it is directed through the opening located at the proximal end of the vessel alignment fitting, through the bore thereof and out the at least one perforation located on the disc-like portion of the fitting aligned with said bore. Thereafter, the blood fills the central bore of the canister until it reaches the cannister outflow fitting located within the cannister cap. Blood which has reached the outflow fitting thence passes through the opening located at the distal end of the fitting, passes through the bore thereof, and out the proximal opening of the fitting. Additional surgical tube 20, connecting the outflow fitting of the cannister cap, is utilized to provide return of blood circulated through the device and vessel maintained therein to a vein within the patient's circulation. As mentioned above, either a pressure regulator, integral to the pump utilized, or a separate pressure regulator, is utilized to maintain pressure entering the harvested vessel from The above-described embodiment of the present invention may be described as an integrated blood flow embodiment of the method of the present invention.

The present invention also contemplates embodiments thereof, wherein, after sufficient blood has been collected from the patient's circulation (as described above, the blood is continually circulated within the flow circuits of the device without return to the patient's own circulatory system. Such embodiments—as illustrated in FIG. 4—may also advantageously utilize a reservoir 26 for containing sufficient blood for circulation as well as a blood heating device 22 so as to maintain the temperature of the blood substantially equal to normal body temperature. The above-described integrated embodiments wherein blood continuously flows from patient to device (and harvested vessel) and back to the patient may obtain the heat required to maintain blood flowing through the harvested vessel at near normal body temperature from the patient's own body. However, non-integrated embodiments of the present invention which do not remain connected to a patient's circulation after initial "filling" of the system will continuously lose heat without the aforementioned additional heating device. These devices enable maintenance of blood temperature at about 40° C. and, of course, have overheat controls preventing blood from heating beyond 43° C. Blood warmers such as the "Fluido" device (Fluido b.v., The Surgical Company) are especially useful in that they combine both accurate temperature control and monitoring functions.

Although the devices disclosed in the '528 application and illustrated herein in FIGS. 1-4 are well suited for practicing the methods of the present invention, other devices demonstrating different designs and configurations are also well suited for the present methods. What is required of all devices in order to practice the methods of the present invention is that such devices: a. include a means for fixing, to a stationary position, one end of a harvested vessel; b. a means of enabling the harvested vessel to freely move and extend to the vessel's full length; c. a means to direct a pulsatile flow of blood through the lumen of the harvested vessel—from that end of the vessel that is fixed to a stationary position to that end of the vessel which is free to extend—; d. a means to cause pulsatile blood to fill the lumen of the vessel and exit from the free end thereof; e. a means to cause the blood exiting the vessel to bathe the outer surface of the blood vessel with circulating blood; and f. a means of returning the pulsatile blood to the fixed end of the vessel (lumen) to provide a complete flow circuit.

As disclosed in FIGS. 1-4, a means to affix one end of a harvested vessel to a stationary position may be provided by the illustrated vessel engagement fitting. However, any means of stabilizing the position of one end of the vessel, including, for example, attaching the end of the vessel directly to surgical tubing (conveying the pulsatile stream of blood), attaching the end of the vessel to a double ended barb which engages both the vessel and a length of surgical tubing, use of a surgical coil to affix the vessel's position, etc. In regard to the freely moving and extending attachment point, the alignment fitting shown in the figures certainly enables a harvested vessel to extend freely within a container while also aligning the vessel. However, the design and configuration of the vessel alignment fitting and the container in which the vessel is bathed may be any configuration or design which provides such free extension/alignment and enables bathing of the outside of the vessel (respectively).

The devices illustrated in FIGS. 5-13 show devices demonstrating further configurations that are well suited for practicing the methods of the present invention.

Figure 5:
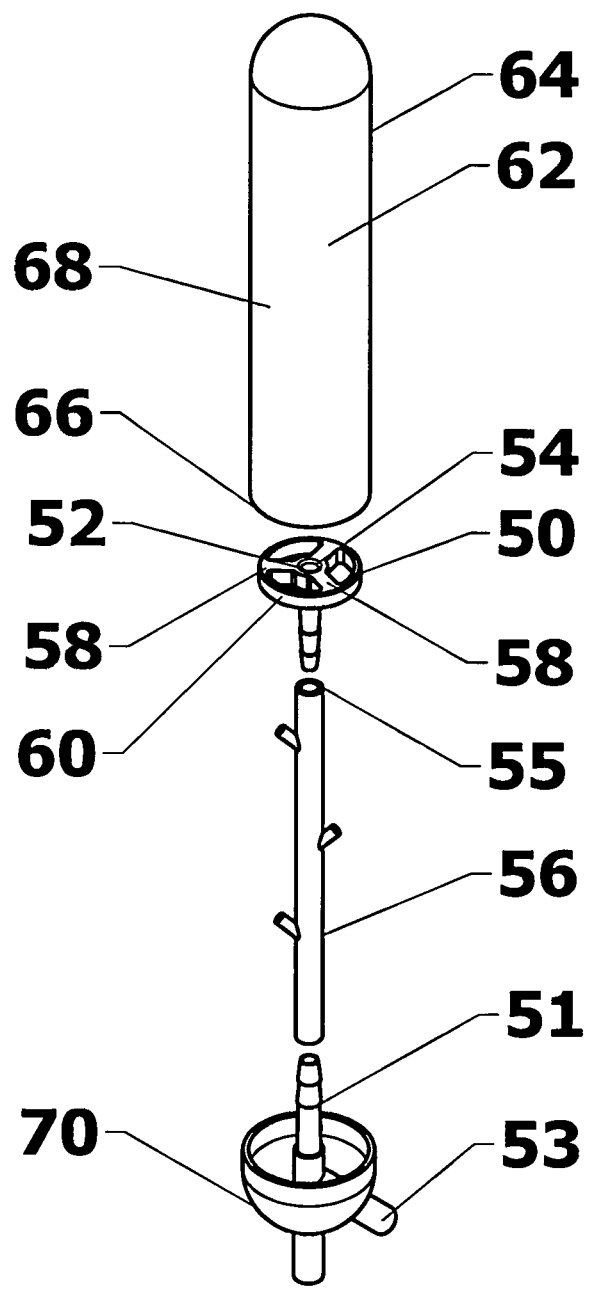
FIG. 5 is an exploded view of an alternate device configured and adapted for practicing the methods of the present invention.

FIG. 5 shows a device utilizing a non-stationary vessel attachment fixture 50 having only one perforation 52 and central bore 54 in fluid connection with the central bore 55 of the harvested vessel 56. The illustrated non-stationary vessel attachment means incorporates three spokes 58 running from the center of the attachment to a wheel-like portion 60. The wheel-like portion is so shaped in order to cause the non-stationary attachment means to easily move up and down the central bore 62 of the vessel cannister 64 which is configured in a test-tube like shape have only the proximal end 66 thereof open. The wheel-like portion 60 of the non-stationary attachment fixture is so shaped due to the round inner walls of the vessel cannister 68. However, as shown below, the general shape of the non-stationary attachment fixture varies in accordance with the shape of the vessel container. Likewise, the cannister cap 70 shown in FIG. 5 is also configured to adapt to and provide a fluid-tight seal with the rounded configuration of the proximal end 66 of the vessel cannister 64. However, there is no constraint upon the shape of the vessel cannister as it may assume any shape that is capable of providing the above-described bathing and circulating functions. As the shape of the canister changes, it is anticipated, as described and illustrated below, the shape of both the non-stationary vessel attachment fixture and means utilized to seal the cannister will also change.

Figure 6:
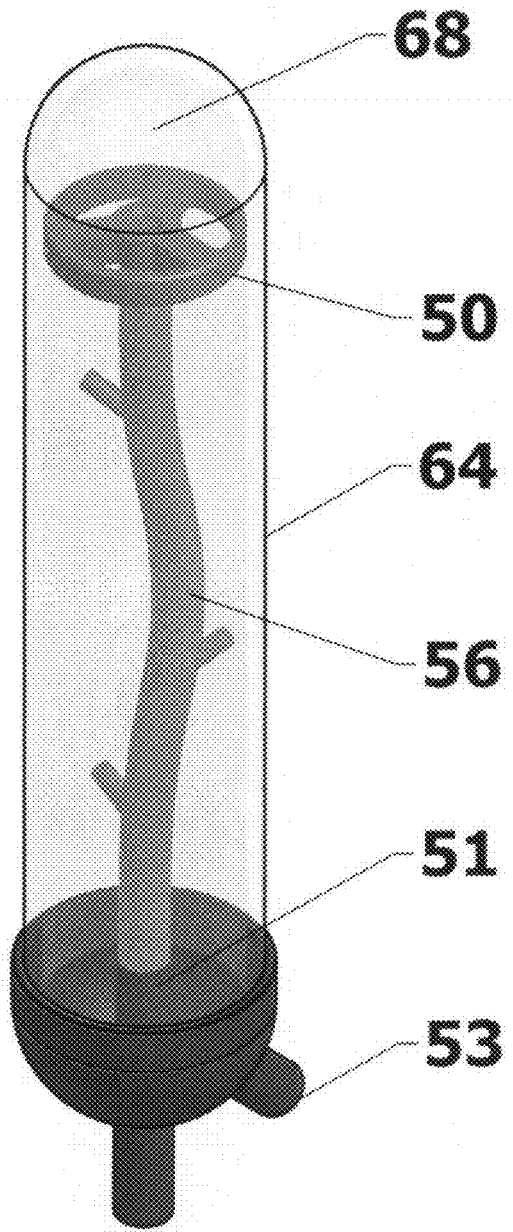
FIG. 6 is a front elevated view of the device illustrated in FIG. 5.
Figure 7:
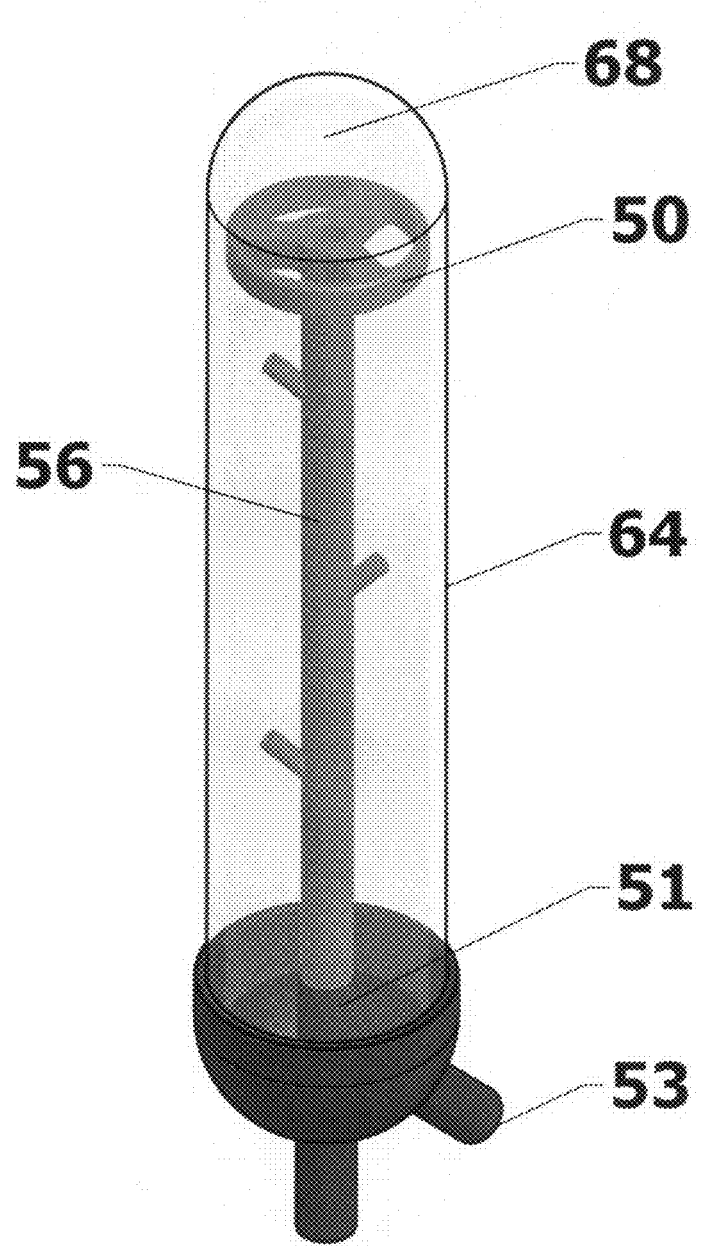
FIG. 7 is a front elevated view of the device illustrated in FIG. 5.

FIG. 6 illustrates the same vessel preservation device as shown I FIG. 5. The vessel 56 illustrated in FIG. 6 includes bends as are found in a vessel attached to the device prior to providing a flow of pulsatile blood through the lumen of the vessel (which exits the single central perforation 52 of the illustrated non-stationary fixture in accordance with the methods of the present invention.). The vessel 56 is thus in the configuration it assumes before a stream of pulsatile blood has filled the lumen and caused it to reach its full natural length. As compared to FIG. 6, FIG. 7 shows the same device with the blood vessel in the extended and straight configuration it assumes after the central lumen of the vessel has be filled with a pulsatile stream of blood. Similar to the device shown in FIG. 1, above, once blood has filled the lumen of the vessel, it exits the vessel through the central bore of the non-stationary attachment fixture 50, fills the bore of the central lumen of the canister 68, and thereafter exits the container via outlet fitting 53. Further examination of FIG. 6 shows the non-stationary vessel attachment fixture 50 in a more proximal position than is shown in FIG. 7. This change in position represents a like change in position that occurs as the lumen of a vessel is filled with blood in accordance with the methods of the present invention. Under such conditions, the non-stationary vessel fixture allows and assists the vessel to extend to its full natural length while, at the same time, aligning the vessel with the longitudinal axis of the canister's central bore. In doing such, the non-stationary vessel fixture moves distally, away from the stationary attachment fixture 51. The more proximal position of the non-stationary fixture as illustrated in FIG. 6 is expected when the vessel lumen is not filled with blood.

Figure 8:
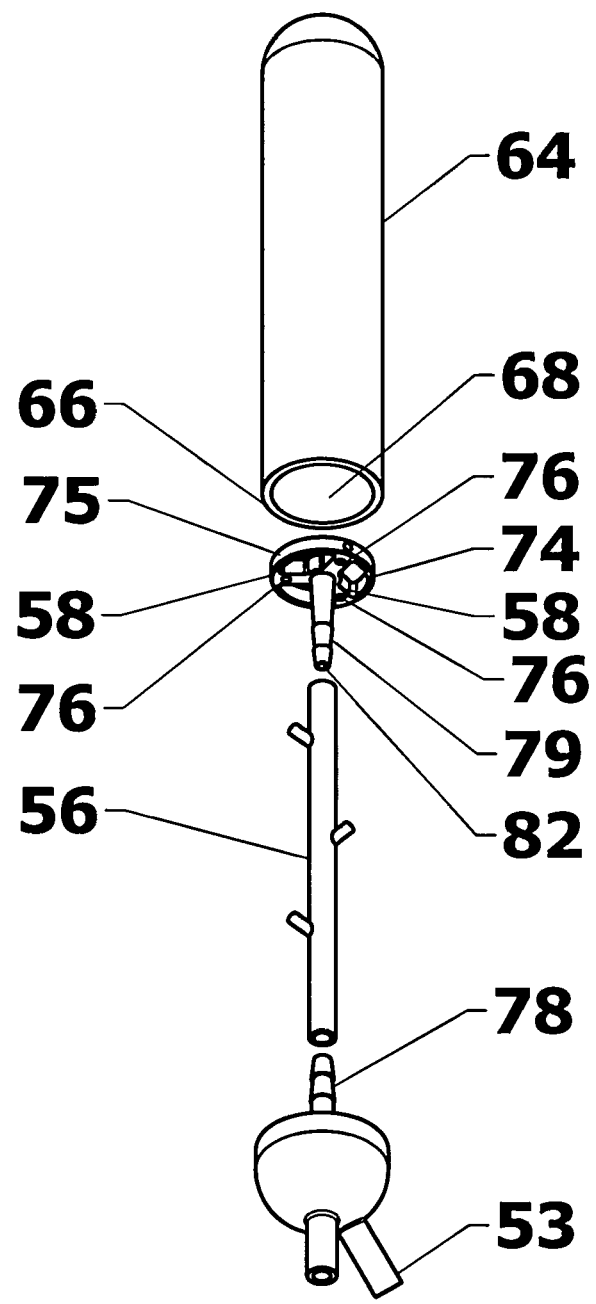
FIG. 8 is an exploded view of a further alternate device configured and adapted for practicing the methods of the present invention.

FIG. 8 illustrates still another device configured and adapted for practicing the methods of the present invention. The non-stationary attachment fixture 74 illustrated in this figure includes openings 76 facing proximally, towards, the fixed end of the vessel attached to the stationary attachment fixture 78. These openings, are configured to be in fluid communication with bores prepared and running within the three spokes 58. The bores prepared within the spokes, in turn, communicate with a central bore formed within the tube-like section 79 and proximal opening 82 of this non-stationary attachment fixture. Such communication enables a pulsatile flow of blood steaming out of the distal end 57 of the harvested vessel (after a flow of such blood has entered the vessel lumen proximal to the end of the vessel affixed to the stationary attachment fixture) to be ejected through these openings 76. This stream of proximally directed blood exiting these three opening 76 provides both enhanced circulation of blood over the outside of the contained vessel as well as aiding in the extension of the vessel by propelling the non-stationary fixture in a distal direction. The outer wheel-like portion 75 of the non-stationary fixture is especially shaped and adapted to enable the fixture to mate with and slide along the curved inner walls of the vessel canister 68.

Figure 9:
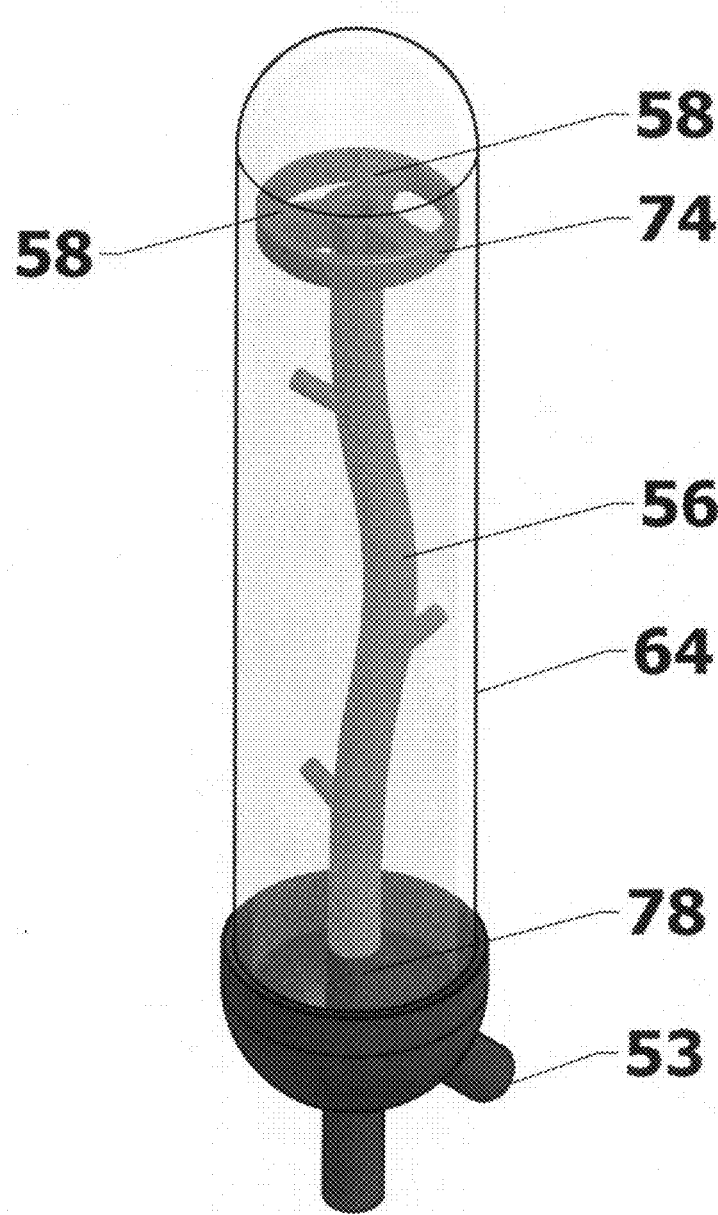
FIG. 9 is a front elevated view of the device illustrated in FIG. 8.
Figure 10:
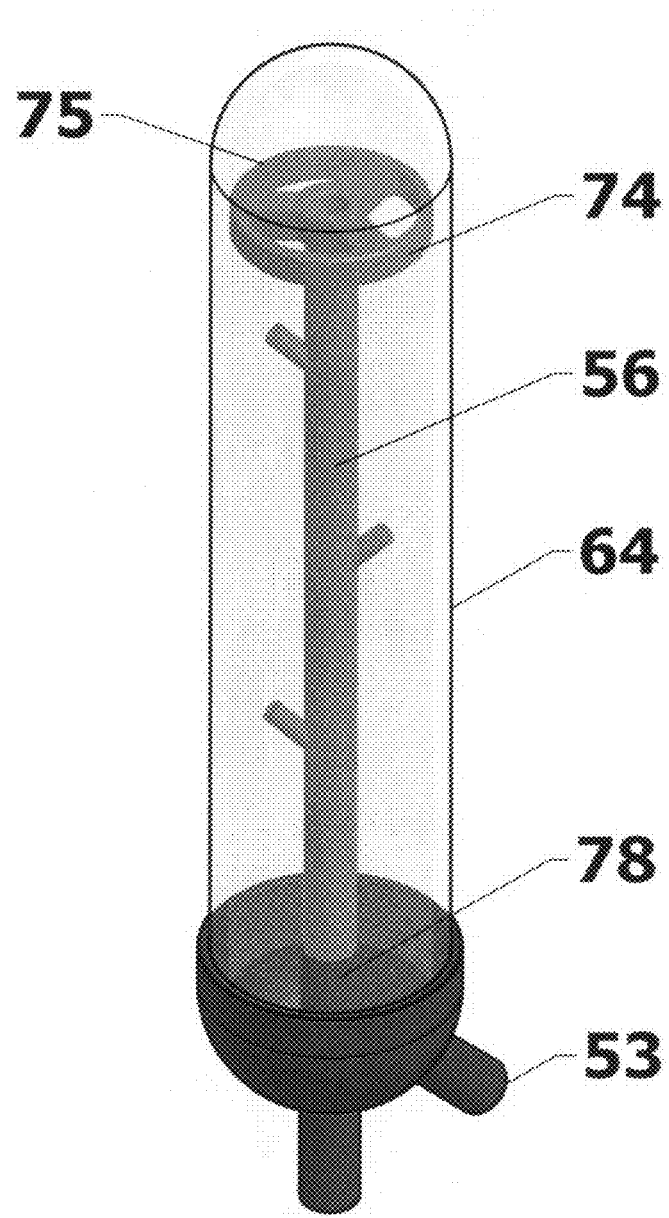
FIG. 10 is a front elevated view of the device illustrated in FIG. 9.

FIGS. 9 and 10 illustrate the same device illustrated in FIG. 8 which is, as discussed above, a device especially configured and adapted to practice the methods of the present invention. In FIG. 9, the vessel configuration is shown as would be expected prior to the application of a pulsatile stream of blood through the stationary attachment fixture 78 and thereafter through the lumen of the vessel (and out from the non-stationary attachment fixture openings 76. More specifically, in this configuration, the vessel 56 shows a curved shape indicative that the lumen of the vessel is not in alignment with the longitudinal axis of the container 64 and the vessel has not assumed its full length. In contrast, FIG. 10 illustrates the expected configuration of the contained vessel 56 after such flow has commenced. In this configuration, the non-stationary attachment fixture 74 has moved distally along with the end of the vessel to which it is affixed so as to assist the vessel, and the lumen therewithin, to assume a the aligned configuration and full length discussed above.

FIG. 10 illustrates still another device having a configuration and design which may be advantageously utilized in practicing the methods of the present invention. The vessel container 84 shown in FIG. 9 is shaped and configured as a rectangular box. Although this particular container demonstrates a rectangular box configuration, and the devices discussed above demonstrate a test-tube like container shape, any container shape capable of containing a blood vessel and the circulating blood described herein, while allowing the vessel to freely extend at one end may be equally utilized. Although the container illustrated in FIG. 10 is formed with an open proximal end 86 and open distal end 88, the distal end is effectively fluidly sealed in the device illustrated by means of an end cap 90. However, the illustrated vessel container may also be fabricated in such a manner as to demonstrate a closed distal end. The opposite (proximal) end of the device 86 is provided with a port cap 91 which provides a site for the positioning of the stationary attachment fixture 92 and an outlet 94. As shown in this figure, and, as discussed above, the shape of the vessel container in this design configuration is a rectangular box. Such a shape includes a central bore 96 having a square cross sectional shape which provides the same containment, circulation and vessel bathing functions as discussed above and required by the methods of the present invention. However, in order to take full advantage of the rectangular configuration of this particular container embodiment and the square cross sectional shape of the central bore therewithin, the non-stationary attachment fixture 96 in this device is shaped so as to demonstrate a square outline. Such an outline mates well with the square cross sectional shape of the central bore 97 of the container and facilitates both the movement of the non-stationary attachment fixture along the length of the central bore of the container, as well as the longitudinal alignment of the contained vessel as discussed above. The illustrated non-stationary attachment fixture contains a single distal opening 99 which is in fluid communication with a central bore running the length of a tube-like portion 101 and a proximal opening 103. The fluid communication of the distal opening, central bore and proximal opening of the non-stationary fixture illustrated in FIGS. 10 (11 & 12) provides a conduit for blood exiting the lumen of the harvested vessel 56 to enter the central bore of the container 96 bathe the outside surface of vessel 56 and then exit the container through outlet fitting 100 to provide the required circulation provided by the methods of the present invention. Although this close adaptation of the outer perimeter shape of the non-stationary fixture with the inner walls (square configuration) of the container's central bore enhance such alignment, such correspondence of shape is not required in order to practice the methods of the present invention. In contrast, the vessel container port cap 91 and end cap 90 necessarily demonstrate a square shape in order to provide the sealing functions required of these elements. Port cap 91 includes, fitted therewithin, stationary attachment fitting 92 and outlet fitting 100 which provide the stationary conduit for providing the pulsatile flow of blood to the contained vessel and a means for the circulating blood to exit the container, respectively.

Figure 11:
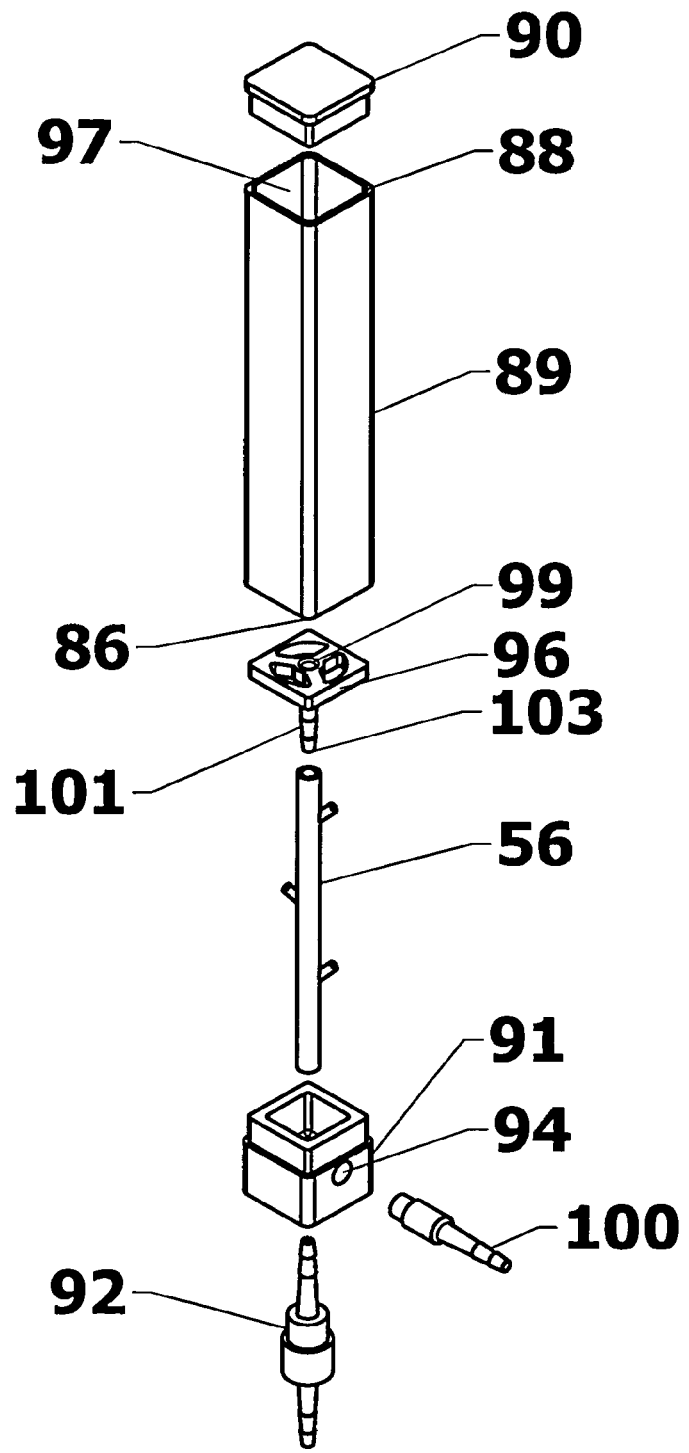
FIG. 11 is an exploded view of a still further alternate device configured and adapted for practicing the methods of the present invention.
Figure 12:
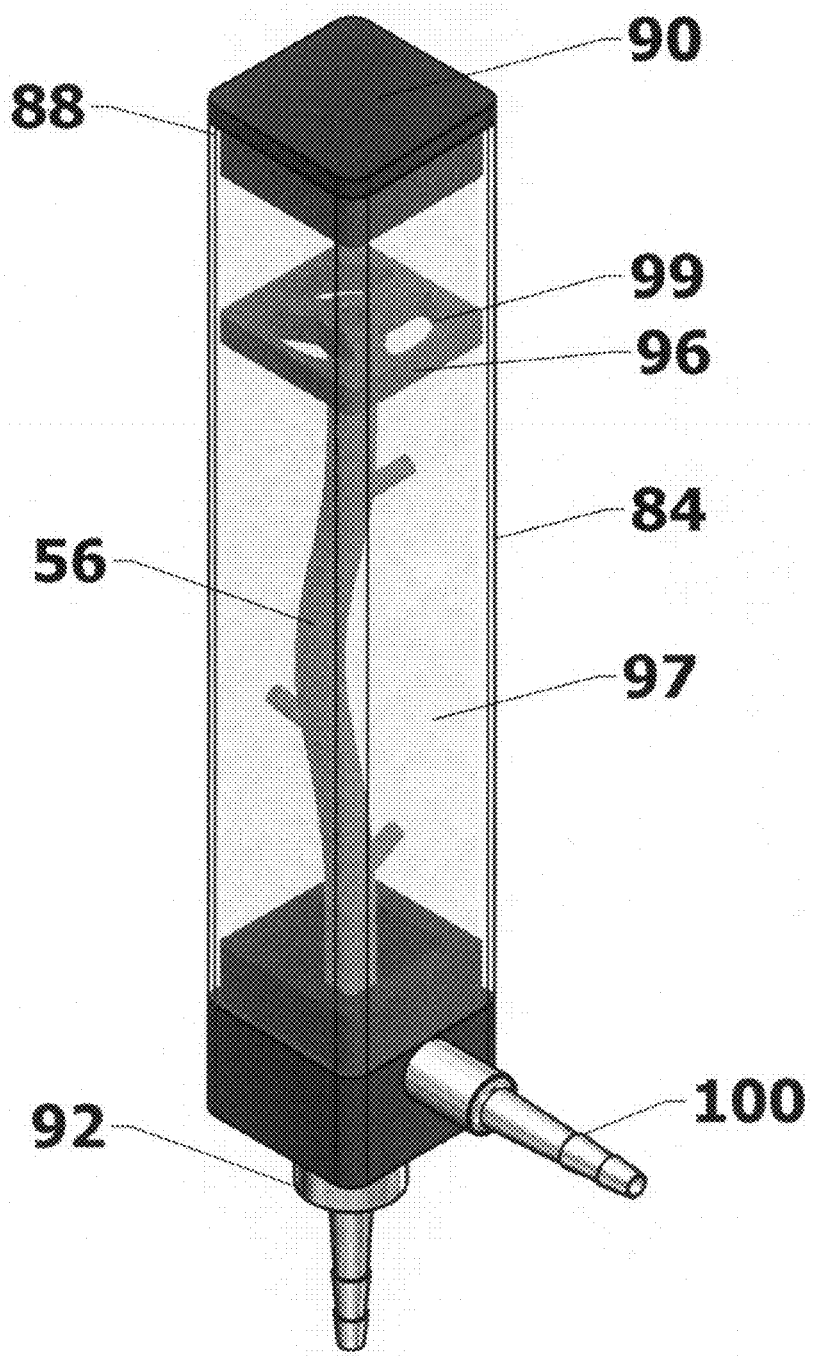
FIG. 12 is a front elevated view of the device illustrated in FIG. 11.
Figure 13:
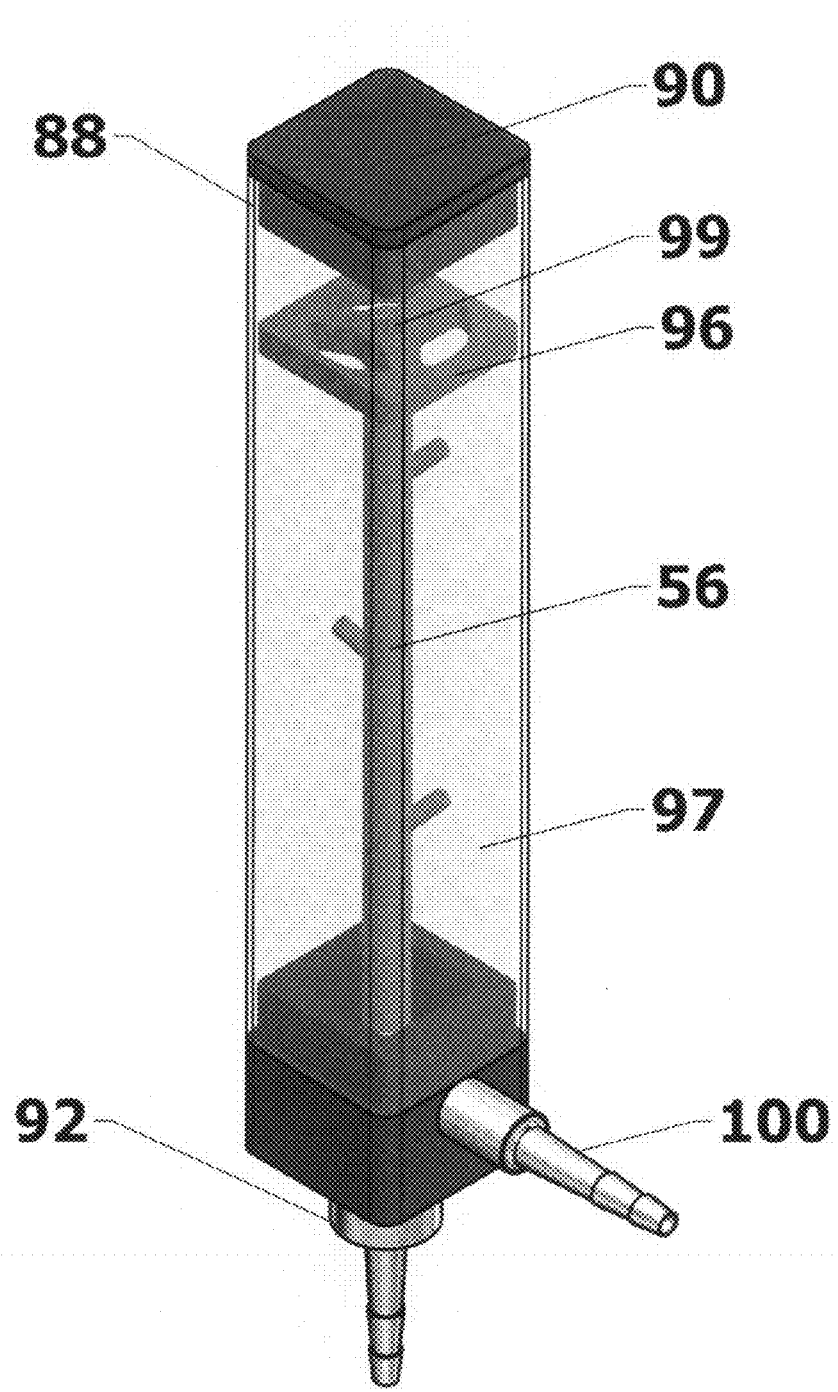
FIG. 13 is a front elevated view of the device illustrated in FIG. 12.

FIG. 11 and FIG. 12 show the same device illustrated in FIG. 10. The vessel 56 illustrated in FIG. 11 is in the configuration one would expect prior to the application of a flow of pulsatile blood to and through the lumen of the vessel. More specifically, vessel 56 as shown in FIG. 11 includes curves representative of a lumen which is not in straight alignment and a vessel devoid of the natural internal pressure provided to the vessel in natural circulation. In contrast, FIG. 12 illustrates the vessel 56 in the configuration one would expect after the pulsatile stream of blood is circulated through and has filled the lumen thereof. As can be noted by examining both figures, the position of the non-stationary attachment fixture in FIG. 11 is proximal to that found in FIG. 12. Such a change in position is representative of the extension of the vessel while engaging the method of the present invention.

The terms and expressions which have been employed in the foregoing specification and in the abstract are used therein as terms of description and not limitation, and there is no intention, in the use of such terms and expressions, of excluding equivalents of the features shown and described or portions thereof, it being recognized that the scope of the invention is defined and limited only by the following claims.

I claim:

1. A method of preserving a harvested blood vessel comprising:

harvesting a blood vessel from a patient, the vessel having a length, a longitudinal axis, a proximal terminus, a distal terminus, a lumen, and an outer surface, the proximal terminus of the harvested vessel being that terminus through which blood entered the harvested vessel and the distal terminus being that terminus of the vessel through which blood exited the harvested vessel while the harvested vessel was still within a host's natural circulation;

attaching the proximal terminus of the harvested vessel to a stationary attachment fixture, said fixture having a length, a proximal end, a distal end and a central bore running the length of said stationary fixture, said central bore being continuous with and in fluid communication with openings located at the proximal and distal ends of the stationary fixture so as to form a fluid conduit, wherein, when the proximal terminus of the harvested vessel is attached to the distal end of the stationary fixture, the lumen of the vessel is placed in fluid communication with the distal opening, central bore and proximal opening of the stationary attachment fixture;

attaching the distal terminus of the harvested vessel to a non-stationary fixture having a length, a proximal end, a distal end, and a central bore, said central bore of the non-stationary fixture being continuous with and in fluid communication with openings located at the proximal and distal ends of the non-stationary fixture, wherein, when the distal terminus of the harvested vessel is attached to the proximal end of the non-stationary fixture, the lumen of the vessel is in fluid communication with the proximal opening, central bore and distal opening of the non-stationary fixture;

introducing the non-stationary fixture, harvested vessel and stationary attachment fixture into a central bore of a container having a length, a central bore running the length of the container, a proximal terminus and a distal terminus, the proximal terminus of the container being open and in fluid communication with the central bore of the container and the distal terminus being closed so as to form a fluid tight seal;

securely attaching the stationary attachment fixture to the proximal terminus of the container so as to fix the position of the proximal terminus of the blood vessel affixed thereto while positioning the non-stationary fixture within the central bore of the container in such a manner as to enable the non-stationary fixture and the distal terminus of the vessel attached thereto, to move and freely extend along the length of the central bore of the container;

sealing the proximal terminus of the container so as to form a fluid tight seal for the central bore of the container except for:

maintaining a fluid conduit running from outside of the container through the proximal opening, central bore and distal opening of the stationary attachment fixture to the proximal terminus, lumen and distal terminus of the blood vessel which, in turn, is in fluid communication with the central bore of the container by means of the proximal opening, the central bore and distal opening of the non-stationary fixture; and maintaining a fluid conduit provided by an outlet fitting located at the proximal end of the container adjacent to the stationary attachment fixture, the outlet fitting thereby providing fluid communication from outside of the container to the central bore of the vessel container;

directing a stream of pulsatile blood through the opening located at the proximal end of the stationary attachment fixture so as to cause said stream of pulsatile blood to flow through the conduit formed by the central bore of the stationary attachment fixture, the distal opening thereof, the lumen of the blood vessel, through the conduit formed by the proximal opening, bore and distal opening of the non-stationary attachment fixture, said pulsatile stream of blood thereafter being directed so as to fill said container thereby completely bathing the outside surface of the blood vessel therein with the stream of pulsatile blood before exiting the container through the outlet fitting; and re-circulating the stream of pulsatile blood through the conduit formed by the stationary attachment fixture so as to provide a continuous circulatory path of pulsatile blood; wherein when the pulsatile stream of blood flows through the lumen of the blood vessel, it fills the lumen of the blood vessel and causes the blood vessel to extend to its full natural length as well as to align with a longitudinal axis of the container and, after the pulsatile blood stream has filled the container, it exits the container and is re-circulated through the stationary attachment fixture to form a continuous blood flow circuit.

2. The method of claim 1 further comprising deriving the stream of pulsatile blood from a blood vessel resident within and part of a patient's circulatory system, thereafter directing the pulsatile stream of blood to and through the opening located at the proximal end of the stationary attachment fixture, through the conduit formed by the stationary attachment fixture, thence through the lumen of the harvested vessel mounted thereupon, through the conduit formed by the non-stationary fixture, through the central bore of the container, out through the outlet fitting, and thereafter conducting said stream of pulsatile blood back to the patient's circulatory system.

3. The method of claim 2, wherein the stream of pulsatile blood is assisted by means of a mechanical pulsatile pump.

4. The method of claim 3 further comprising regulating the pressure of the pulsatile stream of blood entering the lumen of the harvested blood vessel by means of a mechanical pressure regulator.

5. The method of claim 3 further comprising regulating the pressure of the pulsatile blood stream to be from about 50 to about 150 mm Hg.

6. The method of claim 1 wherein the pulsatile stream of blood is derived from a blood reservoir and mechanical pulsatile pump and the continuous blood flow circuit is separate and apart from the patient's circulatory system.

7. The method of claim 6 further comprising regulating pressure of the pulsatile stream of blood by means of a mechanical pressure regulator.

8. The method of claim 7 further comprising regulating the pressure of the pulsatile stream of blood to be from about 50 to about 150 mm Hg.

9. The method of claim 8 further comprising heating the pulsatile stream of blood by means of a mechanical blood warmer.

10. The method of claim 9 further comprising heating the pulsatile stream of blood to a temperature of about 40 degrees centigrade.

11. A method of preserving a harvested blood vessel comprising:

harvesting a blood vessel from a patient, the vessel having a length, a longitudinal axis a proximal terminus, a distal terminus, a lumen, and an outer surface the proximal terminus of the harvested vessel being that terminus through which blood entered the harvested vessel and the distal terminus being that terminus of the vessel through which blood exited the harvested vessel while the harvested vessel was still within a host's natural circulation;

attaching the distal terminus of the harvested vessel to a stationary attachment fixture, said fixture having a length, a proximal end, a distal end and a central bore running the length of said stationary fixture, said central bore being continuous with and in fluid communication with openings located at the proximal and distal ends of the stationary fixture so as to form a fluid conduit, wherein, when the distal terminus of the harvested vessel is attached to the distal end of the stationary fixture, the lumen of the vessel is placed in fluid communication with the distal opening, central bore and proximal opening of the stationary attachment fixture;

attaching the proximal terminus of the harvested vessel to a non-stationary fixture having a length, a proximal end, a distal end, and a central bore, said central bore of the non-stationary fixture being continuous with and in fluid communication with openings located at the proximal and distal ends of the non-stationary fixture, wherein, when the proximal terminus of the harvested vessel is attached to the proximal end of the non-stationary fixture, the lumen of the vessel is in fluid communication with the proximal opening, central bore and distal opening of the non-stationary fixture;

introducing the non-stationary fixture, harvested vessel and stationary attachment fixture into a central bore of a container having a length, a central bore running the length of the container, a proximal terminus and a distal terminus, the proximal terminus of the container being open and in fluid communication with the central bore of the container and the distal terminus being closed so as to form a fluid tight seal;

securely attaching the stationary attachment fixture to the proximal terminus of the container so as to fix the position of the distal terminus of the blood vessel affixed thereto while positioning the non-stationary fixture within the central bore of the container in such a manner as to enable the non-stationary fixture and the proximal terminus of the vessel attached thereto, to move and freely extend along the length of the central bore of the container;

sealing the proximal terminus of the container so as to form a fluid tight seal for the central bore of the container except for:

maintaining a fluid conduit running from outside of the container through the proximal opening, central bore and distal opening of the stationary attachment fixture to the distal terminus, lumen and proximal terminus of the blood vessel which, in turn, is in fluid communication with the central bore of the container by means of the proximal opening, the central bore and distal opening of the non-stationary fixture; and maintaining a fluid conduit provided by an outlet fitting located adjacent to the stationary attachment fixture, the outlet fitting thereby providing fluid communication from outside of the container to the central bore of the vessel container;

directing a stream of pulsatile blood through the opening located at the proximal end of the stationary attachment fixture so as to cause said stream of pulsatile blood to flow through the conduit formed by the central bore of the stationary attachment fixture, the distal opening thereof, the lumen of the blood vessel, through the conduit formed by the proximal opening, bore and distal opening of the non-stationary attachment fixture, said pulsatile stream of blood thereafter being directed so as to fill said container thereby completely bathing the outside surface of the blood vessel therein with the stream of pulsatile blood before exiting the container through the outlet fitting; and re-circulating the stream of pulsatile blood through the conduit formed by the stationary attachment fixture so as to provide a continuous circulatory path of pulsatile blood; wherein when the pulsatile stream of blood flows through the lumen of the blood vessel, it fills the lumen of the blood vessel and causes the blood vessel to extend to its full natural length as well as to align with a longitudinal axis of the container and, after the pulsatile blood stream has filled the container, it exits the container and is re-circulated through the stationary attachment fixture to form a continuous blood flow circuit.

12. The method of claim 11 further comprising deriving the stream of pulsatile blood from a blood vessel resident within and part of a patient's circulatory system, thereafter directing the pulsatile stream of blood to and through the opening located at the proximal end of the stationary attachment fixture, through the conduit formed by the stationary attachment fixture, thence through the lumen of the harvested vessel mounted thereupon, through the conduit formed by the non-stationary fixture, through the central bore of the container, out through the outlet fitting, and thereafter conducting said stream of pulsatile blood back to the patient's circulatory system.

13. The method of claim 12, wherein the stream of pulsatile blood is assisted by means of a mechanical pulsatile pump.

14. The method of claim 13 further comprising regulating the pressure of the pulsatile stream of blood entering the lumen of the harvested blood vessel by means of a mechanical pressure regulator.

15. The method of claim 12 further comprising regulating the pressure of the pulsatile blood stream to be from about 50 to about 150 mm Hg.

16. The method of claim 11 wherein the pulsatile stream of blood is derived from a blood reservoir and mechanical pulsatile pump and the continuous blood flow circuit is separate and apart from the patient's circulatory system.

17. The method of claim 16 further comprising regulating pressure of the pulsatile stream of blood by means of a mechanical pressure regulator.

18. The method of claim 17 further comprising regulating the pressure of the pulsatile stream of blood to be from about 50 to about 150 mm Hg.

19. The method of claim 18 further comprising heating the pulsatile stream of blood by means of a mechanical blood warmer.

20. The method of claim 19 further comprising heating the pulsatile stream of blood to a temperature of about 40 degrees centigrade.

* * * * *